(12) United States Patent
Atencia et al.

(10) Patent No.: US 12,392,694 B2
(45) Date of Patent: Aug. 19, 2025

(54) APPARATUSES AND METHODS FOR RAPID COLLECTION OF MICROBE FROM A SAMPLE

(71) Applicant: PathOtrak, Inc., College Park, MD (US)

(72) Inventors: Javier Atencia, College Park, MD (US); Ethan Reggia, College Park, MD (US); Drew Tack, College Park, MD (US)

(73) Assignee: PathOtrak Inc., College Park, MD (US)

( * ) Notice: Subject to any disclaimer, the term of this patent is extended or adjusted under 35 U.S.C. 154(b) by 884 days.

(21) Appl. No.: 17/603,248

(22) PCT Filed: Apr. 12, 2020

(86) PCT No.: PCT/US2020/027863
§ 371 (c)(1),
(2) Date: Oct. 12, 2021

(87) PCT Pub. No.: WO2020/210772
PCT Pub. Date: Oct. 15, 2020

(65) Prior Publication Data
US 2022/0178799 A1 Jun. 9, 2022

Related U.S. Application Data

(60) Provisional application No. 62/932,168, filed on Nov. 7, 2019, provisional application No. 62/833,317, filed on Apr. 12, 2019.

(51) Int. Cl.
*B01L 3/00* (2006.01)
*A61B 5/145* (2006.01)
(Continued)

(52) U.S. Cl.
CPC ....... *G01N 1/4077* (2013.01); *C12N 15/1017* (2013.01); *C12Q 1/689* (2013.01); *G01N 2001/4088* (2013.01)

(58) Field of Classification Search
CPC ......... G01N 1/4077; G01N 2001/4088; C12N 15/1017; C12Q 1/689
See application file for complete search history.

(56) References Cited

U.S. PATENT DOCUMENTS

| 3,079,001 A | 2/1963 | Griffith |
| 4,829,002 A | 5/1989 | Pattillo et al. |

(Continued)

FOREIGN PATENT DOCUMENTS

| CA | 3126717 A1 | 7/2020 |
| GB | 2189404 A | 10/1987 |

(Continued)

OTHER PUBLICATIONS

Purchas, D. B. et al., "Handbook of filter media," Handbook of Filter Media, Referex; Elsevier Advanced Technology, Oxford, Oct. 28, 2002, 1-549.

(Continued)

*Primary Examiner* — Jennifer Wecker
*Assistant Examiner* — Oyeleye Alexander Alabi
(74) *Attorney, Agent, or Firm* — COOLEY LLP

(57) ABSTRACT

The present invention provides apparatuses and methods for collecting microbes in a sample. The present invention provides apparatuses, systems, or devices, configured to receive a test sample, comprising one or more sealable containers configured to receive a test sample comprising a liquid portion, at least one outlet port, and comprising at least one filtration filter and at least one concentration filter fluidly connected in sequence to the at least one outlet port to form a filtered outlet port.

26 Claims, 22 Drawing Sheets

(51) Int. Cl.

| | | |
|---|---|---|
| *A61B 5/1477* | (2006.01) | |
| *B01F 33/302* | (2022.01) | |
| *B01F 33/3033* | (2022.01) | |
| *B01L 7/00* | (2006.01) | |
| *B33Y 80/00* | (2015.01) | |
| *C12M 1/00* | (2006.01) | |
| *C12M 1/34* | (2006.01) | |
| *C12M 3/00* | (2006.01) | |
| *C12M 3/06* | (2006.01) | |
| *C12N 15/10* | (2006.01) | |
| *C12Q 1/6848* | (2018.01) | |
| *C12Q 1/686* | (2018.01) | |
| *C12Q 1/689* | (2018.01) | |
| *G01N 1/40* | (2006.01) | |
| *G01N 21/29* | (2006.01) | |
| *G01N 21/77* | (2006.01) | |
| *G01N 21/78* | (2006.01) | |
| *G01N 21/84* | (2006.01) | |
| *G01N 33/493* | (2006.01) | |
| *G01N 33/52* | (2006.01) | |
| *G01N 33/543* | (2006.01) | |
| *G01N 35/00* | (2006.01) | |
| *G06T 7/00* | (2017.01) | |
| *G06T 7/73* | (2017.01) | |
| *G06T 7/90* | (2017.01) | |
| *G16H 10/40* | (2018.01) | |

(56) References Cited

U.S. PATENT DOCUMENTS

| | | | |
|---|---|---|---|
| 5,965,019 | A | 10/1999 | Olsen et al. |
| 6,139,757 | A | 10/2000 | Ohmura et al. |
| 6,274,055 | B1 | 8/2001 | Zuk, Jr. |
| 7,547,526 | B2 | 6/2009 | Ladisch et al. |
| 11,634,782 | B2 | 4/2023 | Stephens |
| 2001/0034058 | A1 | 10/2001 | Kopf |
| 2005/0244943 | A1 | 11/2005 | Ladisch et al. |
| 2006/0199260 | A1 | 9/2006 | Zhang et al. |
| 2010/0084270 | A1 | 4/2010 | Vulto et al. |
| 2010/0255484 | A1 | 10/2010 | Halverson et al. |
| 2011/0059462 | A1 | 3/2011 | Lim et al. |
| 2014/0175029 | A1* | 6/2014 | Niazi ............... C12M 47/02 210/797 |
| 2015/0118688 | A1 | 4/2015 | Weidemaier et al. |
| 2015/0152375 | A1 | 6/2015 | Hedrick et al. |
| 2015/0252314 | A1 | 9/2015 | Onji et al. |
| 2015/0253226 | A1* | 9/2015 | Augustsson ...... B01L 3/502753 435/7.25 |
| 2016/0137970 | A1 | 5/2016 | Hedrick et al. |
| 2017/0022470 | A1 | 1/2017 | Calemczuk et al. |
| 2017/0121758 | A1* | 5/2017 | Atencia-Fernandez ............... G01N 15/06 |
| 2017/0273670 | A1 | 9/2017 | Rostaing et al. |
| 2018/0117236 | A1 | 5/2018 | Zhou et al. |
| 2018/0154286 | A1 | 6/2018 | Dorian |
| 2018/0180611 | A1 | 6/2018 | Ladisch et al. |
| 2018/0230552 | A1* | 8/2018 | Goletz ............... C12Q 1/6806 |
| 2021/0102234 | A1 | 4/2021 | Atrache et al. |
| 2021/0346843 | A1 | 11/2021 | Atencia-Fernandez |

FOREIGN PATENT DOCUMENTS

| | | | |
|---|---|---|---|
| JP | WO2018003476 A1 | 1/2019 | |
| WO | WO-2015187745 A1 | 12/2015 | |
| WO | WO-2018003476 A1 | 1/2018 | |
| WO | WO 2020/051311 A1 | 3/2020 | |
| WO | WO-2020210772 A1 | 10/2020 | |
| WO | WO-2024118996 A2 | 6/2024 | |
| WO | WO-2025049942 A1 | 3/2025 | |

OTHER PUBLICATIONS

Extended European Search Report for Application No. EP20788458. 6, dated Nov. 29, 2022, 10 pages.
Baker, R. W. "7 Microfiltration" In: "Membrane Technology and Applications, Third Edition", Jan. 1, 2012, John Wiley & Sons, Ltd-, XP055213013, ISBN: 978-0-47-074372-0, 303-324.
Brehm-Stecher, et al., "Sample Preparation: The Forgotten Beginning," Journal of Food Protection, 2009, 72(8), 1774-1789.
International Search Report issued in PCT/US2020/027863 dated Jun. 17, 2020, 1-4.
PCT Search Report and Written Opinion issued in connection with corresponding PCT Application No. PCT/US19/49717 mailed on Nov. 19, 2019, 8 pages.
Blasing et al., "Plastics in soil: Analytical methods and possible sources", Science of the Total Environment, 2018, 612:422-435.
Brewster et al., "Large-Volume Filtration for Recovery and Concentration of *Escherichia coli* O157:H7 from Ground Beef", Journal of Rapid Methods & Automation in Microbiology, 2009, 17(2):242-256.
Chen et al., "Mechanistic Study of Membrane Concentration and Recovery of Listeria monocytogenes", Biotechnology and Bioengineering, vol. 89, No. 3, 2005, 263-273.
Extended European Search Report for European Application No. 24196297.6 mailed Feb. 21, 2025, 11 pages.
Fachmann et al., "Detection of Salmonella in meat in less than 5 hours by a low-cost and non-complex sample preparation method", Applied and Environmental Microbiology, 2017, 83(5):1-34.
Faradji et al., "Large scale isolation of human blood monocytes by continuous flow centrifugation leukapheresis and counterflow centrifugation elutriation for adoptive cellular immunotherapy in cancer patients", Journal of immunological methods, 1994, 174(1-2), 3 pages.
Final Office Action for U.S. Appl. No. 17/274,000 dated May 15, 2024, 19 pages.
Fukushima et al., "Rapid Separation and Concentration of Food-Borne Pathogens in Food Samples Prior to Quantification by Viable-Cell Counting and Real-Time PCR", Applied and Environmental Microbiology, 2007, 73(1):92-100.
Hurley et al., "Validation of a Method for Extracting Microplastics from Complex, Organic-Rich, Environmental Matrices", Environmental Science & Technology, 2018, 52(13):7409-7417.
International Preliminary Report on Patentability issued in PCT/US2019/049717 dated Mar. 9, 2021, 6 pages.
International Preliminary Report on Patentability issued in PCT/US2020/027863 dated Sep. 28, 2021, 6 pages.
International Search Report and Written Opinion for International Application No. PCT/US2023/081957 dated May 6, 2024, 18 pages.
International Search Report and Written Opinion for International Application No. PCT/US2024/044724 mailed Jan. 8, 2025, 18 pages.
Invitation to pay additional fees for International Application No. PCT/US2023/081957, dated Feb. 16, 2024, 2 pages.
Invitation to pay additional fees for International Application No. PCT/US2024/044724, mailed Nov. 12, 2024, 2 pages.
Jaffrin, "Dynamic shear-enhanced membrane filtration: A review of rotating disks, rotating membranes and vibrating systems", J. Membr. Sci., 2008, 324:7-25.
Kim et al., "Dynamic microfiltration with a perforated disk for effective harvesting of microalgae", J. Membr. Sci., 2015, 475:252-258.
Non-Final Office Action for U.S. Appl. No. 17/274,000 dated Dec. 26, 2023, 21 pages.
Non-Final Office Action for U.S. Appl. No. 17/274,000 mailed Dec. 6, 2024, 17 pages.
Non-Final Office Action for U.S. Appl. No. 17/274,000 mailed Mar. 6, 2025, 18 pages.
Notice of Acceptance for Australian Application No. 2020271134 mailed Mar. 26, 2025, 3 pages.
Office Action for Australian Application No. 2020271134 mailed Nov. 29, 2024, 3 pages.
Office Action for Australian Application No. AU20190335303 mailed Jul. 3, 2024, 3 pages.

(56) References Cited

OTHER PUBLICATIONS

Office Action for Canadian Application No. 3, 136,712 dated Apr. 17, 2023, 7 pages.
Office Action for Canadian Patent Application No. CA3136712 dated Feb. 16, 2024, 5 pages.
Pessoa et al., "Evaluation of cross-flow microfiltration membranes using a rotary disc-filter", Process Biochem., 1998, 33:39-45.
Rios et al., "Dynamic Microfiltration in Microalgae Harvesting for Biodiesel Production", Ind. Eng. Chem. Res., 2011, 50:2455-2460 (7 pages total).
Sanchez-Nieva et al., "A new analytical technique for the extraction and quantification of microplastics in marine sediments focused on easy implementation and repeatability", Analytical Methods, 2017, 9(45):6371-6378.
Supplemental European Search Report issued in EP Application No. 19858459.1 dated Apr. 20, 2022, 7 pages.
Tiemann et al., "Elutriation: Theoretical Considerations and Methodological Improvements", Marine Ecology—Progress Series, 1979, 1:277-281.
Turpin et al., "Centrifugal elutriation as a method for isolation of large numbers of functionally intact human peripheral blood monocytes", Journal of clinical apheresis, 1986, 3(2):111-118 (2 pages total).
Wang et al., "Culture-Independent Rapid Detection Methods for Bacterial Pathogens and Toxins in Food Matrices", Comprehensive Reviews in Food Science and Food Safety, 2016, 15(1):183-205.
Wolffs et al., "Direct Quantitation and Detection of Salmonellae in Biological Samples without Enrichment, Using Two-Step Filtration and Real-Time PCR", Applied and Environmental Microbiology, 2006, 72(6):3896-3900.

\* cited by examiner

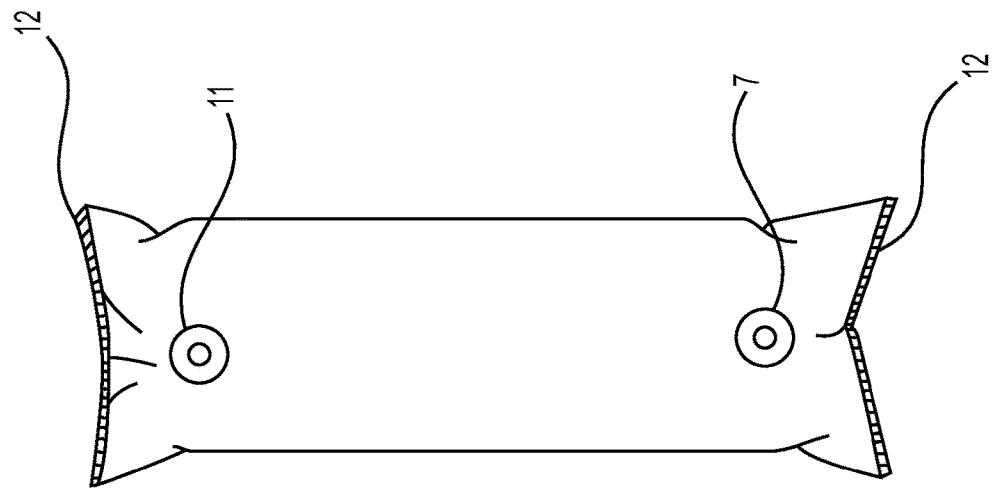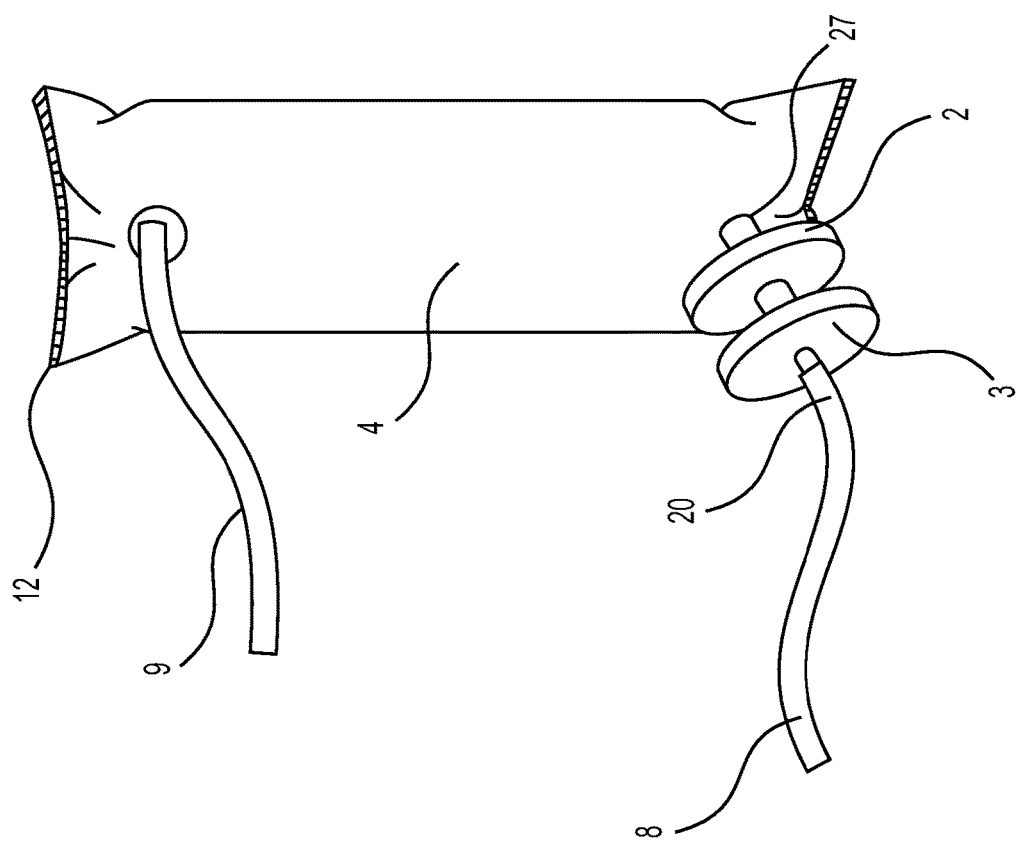
FIG. 3E

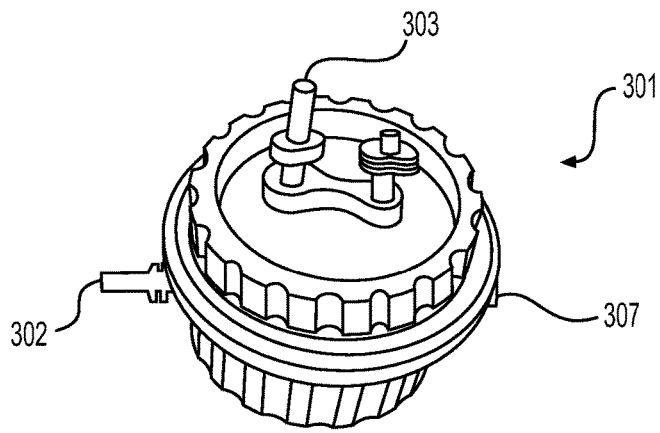
FIG. 8A
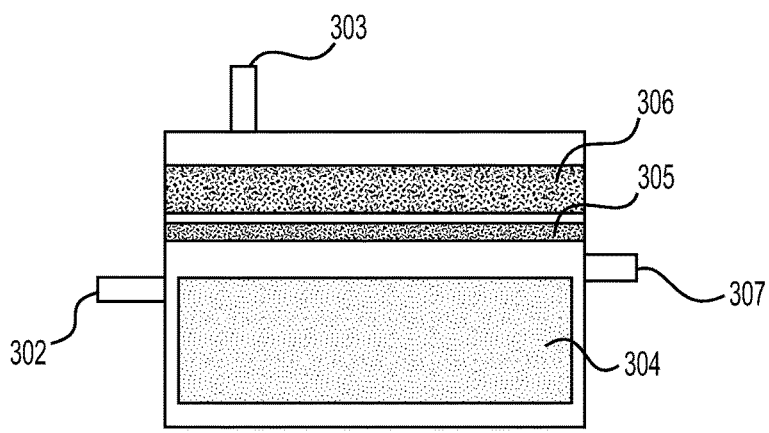
FIG. 8B
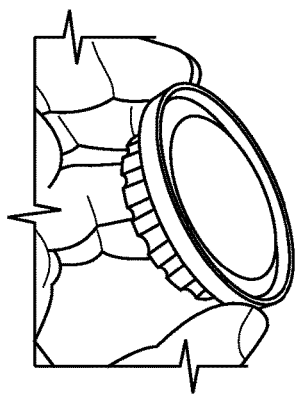
FIG. 9A
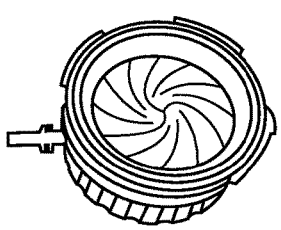
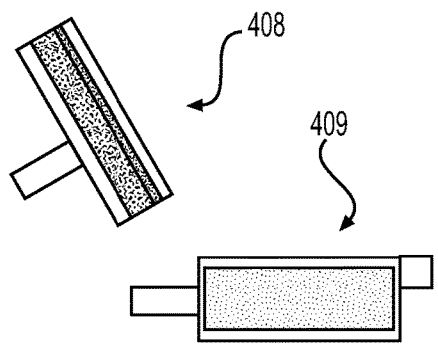
FIG. 9B

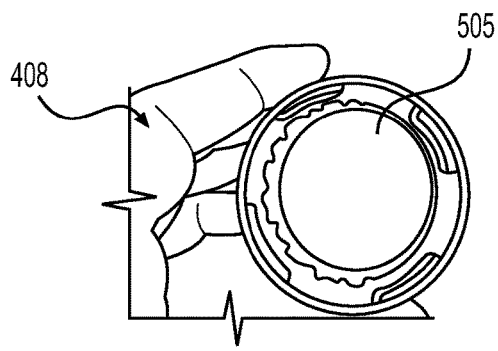
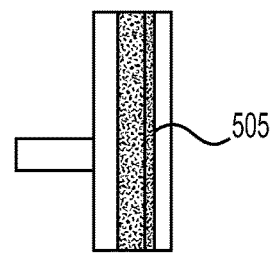
FIG. 10A    FIG. 10B
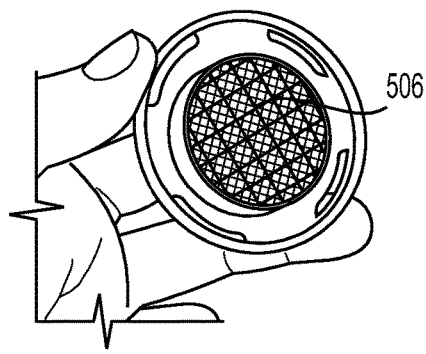
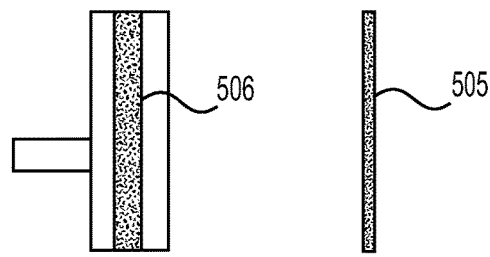
FIG. 10C    FIG. 10D
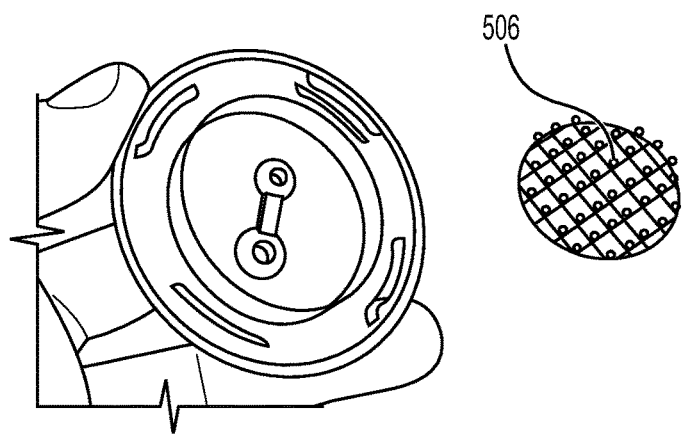
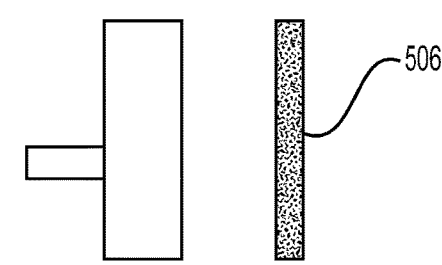
FIG. 10E    FIG. 10F

SALMONELLA IN 325g GROUND BEEF

|   | 1 | 2 | 3 | 4 | 5 | 6 | 7 | 8 | 9 | 10 | 11 | 12 |   |
|---|---|---|---|---|---|---|---|---|---|----|----|----|---|
| A |   |   |   |   |   |   |   |   |   |    |    |    | A |
| B |   | EXT POSITIVE | EXT POSITIVE | -3 5ul POSITIVE | -3 POSITIVE | -4 POSITIVE | -4 POSITIVE | POS CTRL VALID CTRL | NEG CTRL VALID CTRL |    |    |    | B |
| C |   |   |   |   |   |   |   |   |   |    |    |    | C |
| D |   |   |   |   |   |   |   |   |   |    |    |    | D |
| E |   |   |   |   |   |   |   |   |   |    |    |    | E |
| F |   |   |   |   |   |   |   |   |   |    |    |    | F |
| G |   |   |   |   |   |   |   |   |   |    |    |    | G |
| H |   |   |   |   |   |   |   |   |   |    |    |    | H |
|   | 1 | 2 | 3 | 4 | 5 | 6 | 7 | 8 | 9 | 10 | 11 | 12 |   |

| WELL | SAMPLE ID | CQ TARGET | CQ INTERNET CONTROL | RESULT |
|------|-----------|-----------|---------------------|--------|
| B02 | ext | 44.58 | N/A | POSITIVE |
| B03 | ext | 45.04 | N/A | POSITIVE |
| B04 | -3 5ul | 32.57 | 31.41 | POSITIVE |
| B05 | -3 | 32.29 | 31.31 | POSITIVE |
| B06 | -4 | 34.79 | 31.8 | POSITIVE |
| B07 | -4 | 34.24 | 31.69 | POSITIVE |
| B08 | POS CTRL | 31.08 | 31.94 | VALID CTRL |
| B09 | NEG CTRL | N/A | 32.13 | VALID CTRL |

E. COLI 0157:H7 & SALMONELLA IN 25g LETTUCE

E. COLI IN 25g LETTUCE

|   | 1 | 2 | 3 | 4 | 5 | 6 | 7 | 8 | 9 | 10 | 11 | 12 |
|---|---|---|---|---|---|---|---|---|---|----|----|----|
| A |   |   |   |   |   |   |   |   |   |    |    |    |
| B |   | BLANK NEGATIVE | -5 5ul NEGATIVE | -5 NEGATIVE | -4 POSITIVE | -3 POSITIVE | POS CTRL VALID CTRL | NEG CTRL VALID CTRL |   |    |    |    |
| C |   |   |   |   |   |   |   |   |   |    |    |    |
| D |   |   |   |   |   |   |   |   |   |    |    |    |
| E |   |   |   |   |   |   |   |   |   |    |    |    |
| F |   |   |   |   |   |   |   |   |   |    |    |    |
| G |   |   |   |   |   |   |   |   |   |    |    |    |
| H |   |   |   |   |   |   |   |   |   |    |    |    |

| WELL | SAMPLE ID | CQ TARGET | CQ INTERNET CONTROL | RESULT |
|------|-----------|-----------|---------------------|--------|
| C02 | BLANK | N/A | 32.16 | NEGATIVE |
| C03 | -5 5ul | N/A | 32.21 | NEGATIVE |
| C04 | -5 | N/A | 36.11 | NEGATIVE |
| C05 | -4 | 40.43 | 36.92 | POSITIVE |
| C06 | -3 | 35.06 | 33.21 | POSITIVE |
| C07 | POS CTRL | 30.43 | 31.86 | VALID CTRL |
| C08 | NEG CTRL | N/A | 32.18 | VALID CTRL |

SALMONELLA IN 25g LETTUCE

|   | 1 | 2 | 3 | 4 | 5 | 6 | 7 | 8 | 9 | 10 | 11 | 12 |   |
|---|---|---|---|---|---|---|---|---|---|----|----|----|---|
| A |   |   |   |   |   |   |   |   |   |    |    |    | A |
| B |   | BLANK NEGATIVE | -5 POSITIVE | -4 POSITIVE | -3 POSITIVE | POS CTRL VALID CTRL | NEG CTRL VALID CTRL |   |   |    |    |    | B |
| C |   |   |   |   |   |   |   |   |   |    |    |    | C |
| D |   |   |   |   |   |   |   |   |   |    |    |    | D |
| E |   |   |   |   |   |   |   |   |   |    |    |    | E |
| F |   |   |   |   |   |   |   |   |   |    |    |    | F |
| G |   |   |   |   |   |   |   |   |   |    |    |    | G |
| H |   |   |   |   |   |   |   |   |   |    |    |    | H |
|   | 1 | 2 | 3 | 4 | 5 | 6 | 7 | 8 | 9 | 10 | 11 | 12 |   |

| WELL | SAMPLE ID | CQ TARGET | CQ INTERNET CONTROL | RESULT |
|---|---|---|---|---|
| C02 | BLANK | N/A | 32.45 | NEGATIVE |
| C03 | -5 | 37.48 | 32.87 | POSITIVE |
| C04 | -4 | 40.16 | 32.92 | POSITIVE |
| C05 | -3 | 34.61 | 32.43 | POSITIVE |
| C06 | POS CTRL | 30.51 | 31.61 | VALID CTRL |
| C07 | NEG CTRL | N/A | 32.08 | VALID CTRL |

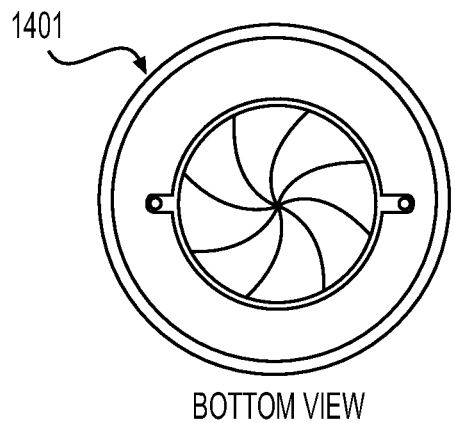
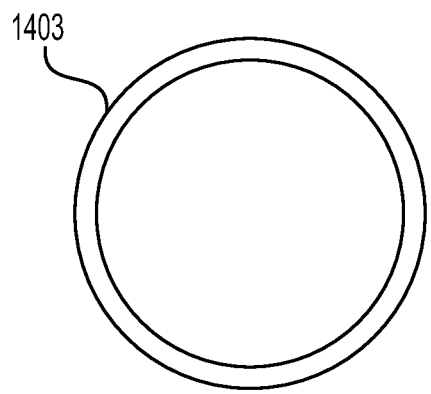
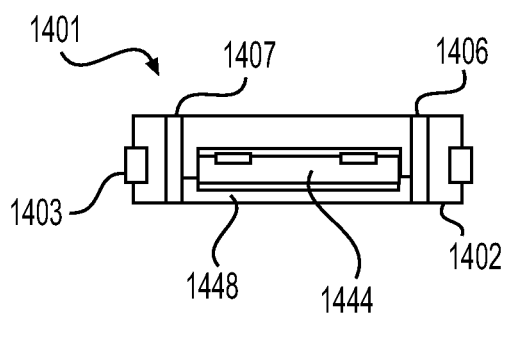
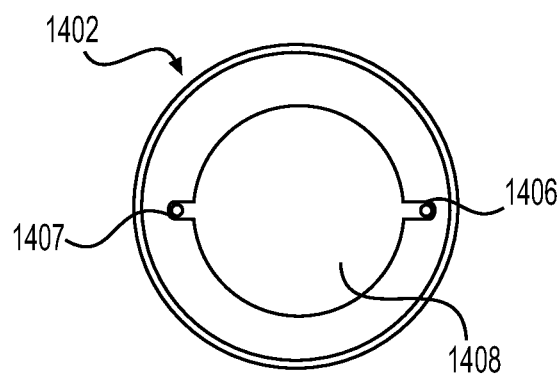
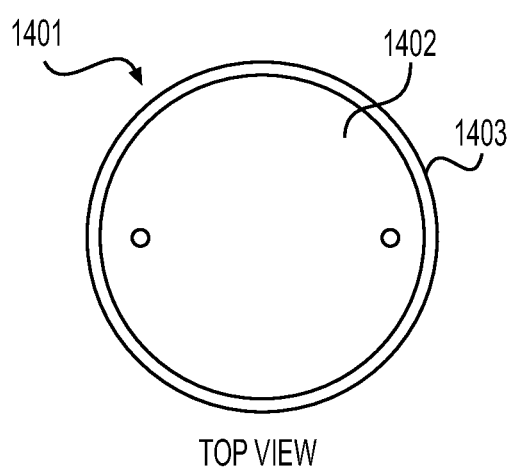
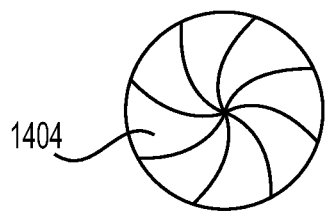
FIG. 19A  FIG. 19B

APPARATUSES AND METHODS FOR RAPID COLLECTION OF MICROBE FROM A SAMPLE

CROSS-REFERENCE TO RELATED APPLICATIONS

This application is a U.S. National Stage Application under 35 U.S.C. § 371 of International PCT Application No. US2020/027863, filed on Apr. 12, 2020, which claims priority to and benefit of U.S. Provisional Application No. 62/833,317, filed on Apr. 12, 2019 and U.S. Provisional Application No. 62/932,168, filed on Nov. 7, 2019, the contents of which are incorporated by reference in their entirety.

FIELD OF THE INVENTION

The present invention generally relates to apparatuses, devices, systems, and methods for collecting microbes from a sample.

BACKGROUND OF THE PRESENT DISCLOSURE

Foodborne illnesses, caused by various microbes contaminating food, affect 1 in 6 Americans each year according to the Centers for Disease Control and Prevention (CDC). The spread of foodborne illnesses can be prevented through careful monitoring of food by producers and sellers, and detection of foodborne microbes present in the food processing lots. Unfortunately, detection of foodborne microbes in food using current techniques can be expensive and time consuming, often taking multiple days to obtain results. The resulting delays between processing and sale of certain foods while awaiting results can be problematic, especially with food items such as meat and ready-to-eat food.

The major bottleneck for rapid food-born microbe detection in food samples is the time required for the sample preparation step called "bacterial enrichment" (Brehm-Stecher et al., J. Food Prot. 72, 1774-1789 (2009)). Enrichment is the process by which certain amount of a food sample, for example, 25 g of a food sample or 375 g in the case of meats, is diluted in a solution. The solution can be a growth medium for certain microbes. Then the food sample is homogenized and incubated for about 18-36 hours to increase the quantity of the microbe contained therein, such as bacteria. For example, the current tests for bacteria require a lengthy incubation process where a food sample is mixed with bacterial nutrients and incubated for 20 hours to allow the bacterial population to increase to detectable levels.

However, the lengthy incubation time results in refrigerated storage costs for producers and test laboratories, as products will have to be stored for extended period of time waiting on test results. This in turn complicates the production, sample tracking, and shipping logistics, and prevents tests from being performed continually in a single 8 hour shift. In the food safety industry, this creates freshness concerns for the food as well.

Enrichment can overcome the interference of the food matrix during the downstream processes, such as detection. While in the last decade, investment and technical advances have reduced the detection time from days to hours, enrichment time has remained unchanged because of the lack of available technological alternatives.

A new type of filtering concept that combines filtration and elutriation (MACE separation, disclosed in the international application No. PCT/US19/49717, which is incorporated herein by reference in its entirety) can be used to separate microbes such as but not limited to bacteria from complex samples such as ground beef.

The present invention provides for rapid concentration and harvesting microbes, e.g., microbes, such as but not limited to *Salmonella, E. coli* O157:H7, etc. from test samples. For example, the apparatus and methods of the invention may be used to identify microbes from whole food samples in as little as 2-5 hours, providing a significant improvement over traditional methods. The methods described herein have significant commercial, clinical, and/or environmental advantages. The apparatuses and methods of the invention can help quickly identify potential threats to public health by reducing the detection time for foodborne microbes from days to hours. Additionally, the apparatuses and methods of the invention can significantly reduce cost related to warehousing and refrigeration. The present invention can also promote the safety of the food-chain supply by facilitating additional testing on foodborne microbes with short time limits and at lower costs.

SUMMARY OF THE PRESENT DISCLOSURE

The present invention provides apparatuses, systems, or devices, configured to receive a test sample, comprising one or more sealable containers configured to receive a test sample comprising a liquid portion, at least one outlet port, and comprising at least one filtration filter and at least one concentration filter fluidly connected in sequence to the at least one outlet port to form a filtered outlet port. The apparatus is configured to permit flow of the liquid portion of the test sample from the one or more sealable containers through the at least one outlet port into and through the filtered outlet port when a pressure difference of equal to or greater than about 4 pounds per square inch (psi) exists between the one or more sealable containers and the filtered outlet port. In some embodiments, the test sample comprises or is suspected to comprise a microbe. In certain embodiments, each of the at least one filtration filter and at least one concentration filter has a pore size equal to or greater than the average size of the microbe.

The present invention also encompasses methods of concentrating a microbe from a test sample, comprising passing the test sample through an apparatus, system, or device provided herein and collecting the concentrated microbe from the concentration filter.

The present invention further provides a microbe concentrator device comprising (a) a filter located above a disk, (b) one cavity between the filter and the disk, (c) one or more inlets and at least one outlet connected directly to the cavity between the disk and the filter, and (d) at least one additional outlet on the side of the filter away from the disk. In some embodiments of the microbe concentrator device, the filter is a membrane filter.

The present invention also provides methods for concentrating a microbe in a test sample, comprising extracting microbes from the test sample using a Microfiltration Assisted Counter flow Elutriation (MACE) separation system or a filtration system, and concentrating the microbe using a microbe concentrator provided herein.

Additionally, the present invention provides methods for detecting one or more microbes in a test sample, comprising: extracting the one or more microbes from the sample using a MACE separation system or a filtration system, concentrating the one or more microbes using a microbe concentrator provided herein, collecting the one or more microbes from the microbe concentrator, and detecting the presence of the one or more microbes.

BRIEF DESCRIPTION OF THE DRAWINGS

FIG. 3E shows an embodiment in which the flexible sample container 4 is not enclosed in a pressurized chamber but instead is pressurized directly through an air inlet 11.

FIGS. 8A and 8B show a photograph and a schematic illustration of an exemplary dynamic microbe concentrator.

FIGS. 9A and 9B show exemplary two halves of an embodiment of the dynamic microbe concentrator.

FIGS. 10A-10F show exemplary first half of an embodiment of the dynamic microbe concentrator, having a membrane filter.

FIGS. 19A-19B illustrate the cross section, top and bottom view of an embodiment of the concentrator and its parts.

DETAILED DESCRIPTION OF THE DISCLOSURE

I. Devices and Methods

Figure 1:
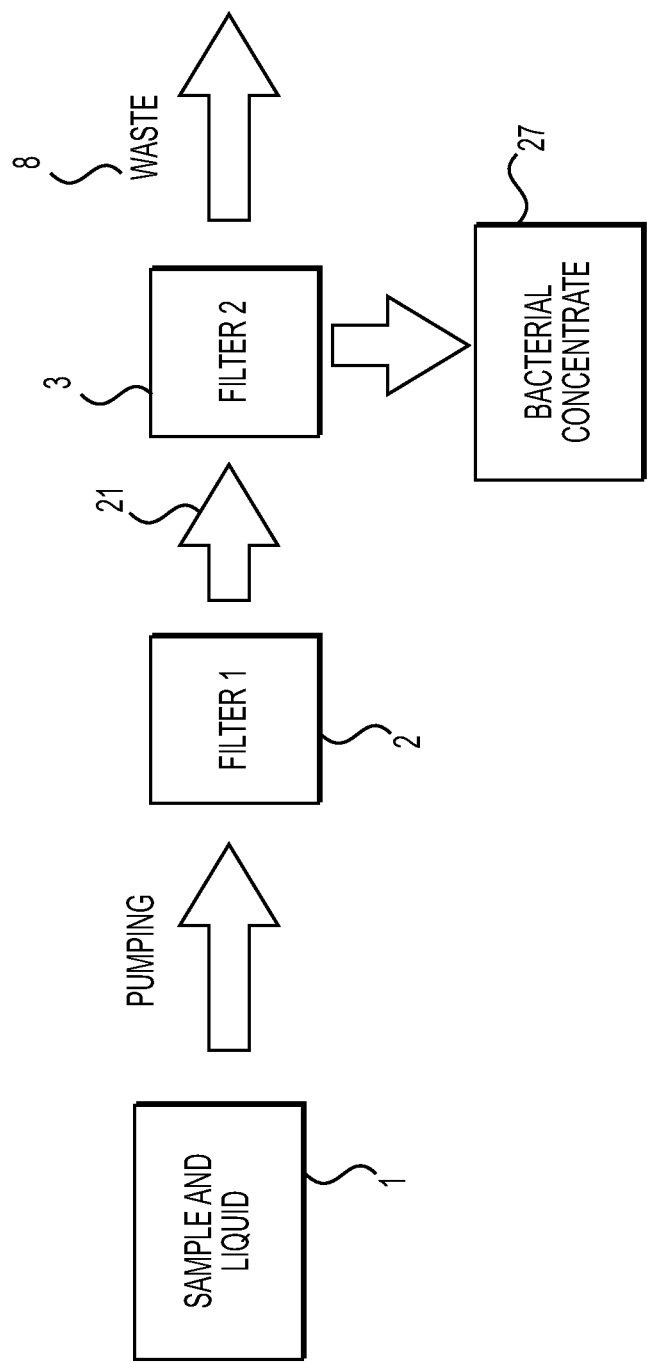
FIG. 1 is a flow chart demonstrating the basic concept of the apparatus and method used for separation, concentration, and harvest of microbes from a test sample.

The present invention provides apparatuses, systems, or devices, comprising one or more sealable containers configured to receive a test sample comprising a liquid portion, at least one outlet port, and at least one filtration filter and at least one concentration filter fluidly connected in sequence to the at least one outlet port to form a filtered outlet port.

As used herein, the terms "apparatus," or "device" are used interchangeably and mean a technical equipment or machinery configured for a particular activity or purpose. In some embodiments, the "apparatus," or "device" can be a complex structure comprising multiple inter-connected components or parts.

As used herein, the term "sample" or "test sample" means any material that contains, or potentially contains, biological material which could contain a microbe. Examples of a sample for use in accordance with the disclosure include, but are not limited to, food samples, patient samples, and environmental samples. Examples of a food sample include, but are not limited to: dairy products such as cheese, yogurt, ice cream or milk, including raw milk; meat such as beef, pork, minced meat, turkey, chicken or other poultry products; ground meat such as ground beef, ground turkey, ground chicken, ground pork; mushrooms, eggs; produce, including fruits and vegetables; peanut butter; seafood products including oysters, pickled salmon or shellfish; or juice, such as fruit or vegetable juice. In one embodiment, the test sample is a vegetable, such as any consumable produce, such as but not limited to lettuce, spinach, kale, broccoli, cauliflower, corn, eggplant, beans, carrots, collards, peas, leaks, onions, cabbage, asparagus, beats, celery, squash, just to name a few. Examples of patient samples include, but are not limited to, feces or body fluids, such as urine, blood or cerebrospinal fluid. Examples of environmental samples include, but are not limited to, drinking water or other fluids, soil samples and non-consumable plant samples. In certain embodiments, the sample must comprise at least a liquid portion. When the starting sample is a solid, such as a consumable vegetable or consumable meat, starting sample is placed in a liquid. The liquid portion of the sample in which the starting sample can be placed is often water or an aqueous-based liquids, such as but not limited to a buffer, or an acid or a base. Examples of aqueous-based liquids include saline, phosphate-buffered solution (PBS), Tris-buffered solution (TBS) and the like. In specific embodiments, the water in which the starting sample material is placed sterilized, or filtered and/or bacteria-free. In additional specific embodiments, the water in which the starting sample material is also or is instead de-ionized. In other embodiments, the liquid portion of the sample in which the starting sample can be placed is an organic-based solvent. In still other embodiments, the liquid portion of the sample in which the starting sample can be placed is a cell-culture medium. When the starting sample material is liquid, the starting sample material may be "diluted" by mixing it with a liquid, such as but not limited to water. In specific embodiments, the test sample is selected from the group comprising water, food sample, human tissue, human fluids, animal tissue, animal fluids, plant tissue, clinical sample, and environmental sample. A test sample may be taken from a source using techniques known to one skilled in the art. In some embodiments, the test sample is a fluid sample. In some embodiments, the test sample can be a solid sample. In some embodiments, the test sample comprises, or can be separated into, fluid portion and sediment particles.

In further embodiments, the test sample may comprise one or more digestive enzymes. Digestive enzymes can digest any small particulates contained in the test sample that may accumulate in the pores of the filters or membranes of the apparatus. Exemplary digestive enzymes include proteinases, proteases, cellulases, etc. The enzymes used are different depending of the type of the test sample.

In further embodiments, the apparatus of the present invention can be used in connection with a flow of a liquid. In other embodiments, the test sample is mixed with a liquid portion.

A culture medium can be any type of medium used in laboratories or in vitro to grow different kinds of microorganisms or cells. A growth or a culture medium is composed of different nutrients that are essential for the growth of the microorganisms or the cells. A growth medium or culture medium can be solid, liquid, or semi-solid. In some embodiments, the culture medium is designed for cell culture. In other embodiments, the culture medium is designed for microbiological culture, which are used for growing microorganisms, such as bacteria or fungi. In some embodiments, the culture media for microorganisms are nutrient broths. In other embodiments, the culture media for microorganisms are agar plates.

A buffered solution is generally an aqueous-based solution consisting of a mixture of a weak acid and its conjugate base, or vice versa. As one of skill in the art will know, buffered solutions can be used to maintain pH at a stable value. Common buffer compounds include, but are not limited to, TAPS ([Tris(hydroxymethyl)methylamino]propanesulfonic acid), Bicine (2-(Bis(2-hydroxyethyl)amino) acetic acid), Tris(Tris(hydroxymethyl)aminomethane) or (2-Amino-2-(hydroxymethyl)propane-1,3-diol), Tricine (3-[N-Tris(hydroxymethyl)methylamino]-2-hydroxypropanesulfonic acid), TAPSO (3-[N-Tris(hydroxymethyl)methylamino]-2-hydroxypropanesulfonic acid), HEPES (4-(2-hydroxyethyl)-1-piperazineethanesulfonic acid), TES (2-[[1,3-dihydroxy-2-(hydroxymethyl)propan-2-yl]amino]ethanesulfonic acid), MOPS (3-(N-morpholino) propanesulfonic acid), PIPES (Piperazine-N,N'-bis(2-ethanesulfonic acid)), Cacodylate (Dimethylarsenic acid), and MES (2-(N-morpholino)ethanesulfonic acid).

As used herein, the term "container" refers to an object that can be used to hold or transport materials, such as the test sample. The containers can be flexible, semi-flexible, intermediate rigid, or rigid. A flexible or semi-flexible container does not have defined shape or can change shape. An intermediate rigid container may have a defined shape but the shape can be changed upon pressure. A rigid container is unable to bend or be forced out of shape. The containers as used herein can be any shape, any size, or any configuration as deemed optimal for use by a person of ordinary skill in the art. The container can be made of any material that is suitable for use in connection with the present invention, including without being limited to, glass, rubber, plastic, polymer, wood, ceramic, metal, paper, a recycled material, a or a material of biological origin. In some embodiments, the container can be made of polyurethane, PVC, nylon, polyethylene, or ethylene propylene (FEP). In a specific embodiment, the container is made of polyethylene. The container can be of any thickness as deemed appropriate by a person skilled in the art, provided that the container is able to withstand pressure being applied to the container without the container bursting, breaking or leaking. In some embodiments, the thickness of the container is between about 1 mil and about 4 mils. In one embodiment, the thickness of the container is about 2 mils. However, containers with a thickness below 1 mil or above 4 mils are also contemplated by the present invention. A "mil" is a unit of thickness equal to one thousandth of an inch (0.001 inch). The container can be disposable or reusable. In some embodiments, the container can be recycled. In some embodiments, the containers can be off-the-shelf products, such as plastic bags, tubes, pouches, jars, or syringes.

The containers used in the apparatuses or methods must be closeable and/or sealable. As used herein, the term closeable means that the one or more openings of a container can be blocked against entry or passage of contents between the inside and outside of the container. A closeable container does not need to be airtight. As used herein, the term sealable means that the one or more openings of a container can be fastened or closed securely to make them impervious, such that the opening cannot be re-opened without damaging the container and/or the inner contents in the container. A sealed container is generally airtight. The sealable container, however, must contain an outlet port. An outlet port is simply an opening in the sealable container. The outlet port of the sealable container, however, will be configured to prevent escape of the sample or the liquid portion of the sample, until pressure is applied to the contents within the sealable container. The methods of closing or sealing a closable or sealable container are generally known and used in the field. Such methods can include but are not limited to, induction, heating, cap, bung, stopper, cork, piston, adhesive, sealant, bodok seal, bonded seal, compression seal fitting, diaphragm seal, glass-to-metal seal, glass-ceramic-to-metal seals, heat seal, hose coupling, hermetic seal, hydrostatic seal, hydrodynamic seal, inflatable seal, labyrinth seal, lid, rotating face mechanical seal, face seal, plug, radial shaft seal, trap, or stuffing box. In one embodiment, the container is a flexible container. For instance, in one specific embodiment, the container is a plastic bag sealed with heat, such as the one depicted in FIG. 2A. In another embodiment, the container is a rigid container, such as the ones depicted in FIGS. 3A-3D. For example, the syringe depicted in 3A may be considered sealable such that reopening the syringe by removing the plunger will disrupt the inner contents.

In some embodiments, the sealable container used in connection with the apparatus comprises at least two opposite walls that define a cavity of the container. In some embodiments, the sealable container comprises two opposite walls that define a cavity of the container. The "opposite walls" need not be perfectly parallel to one another, for example a "plastic bag" comprised of one or two sheets of, e.g. polyethylene, heat-sealed 3 or 4 sides to create "bag" with a defined volume therein. In some embodiments, the sealable container comprises at least four walls that define a cavity of the container. In some embodiments, the sealable container comprises a circular shape, e.g. a cylinder.

As used herein, the term "cavity" refers to an empty space. In some embodiments, a cavity is defined by the walls of the sealable container, for example, as illustrated as 4 in FIG. 2A. In some embodiments, a cavity is defined by one continuous wall, e.g., a cylinder, of the sealable container, for example, as illustrated as 13 in FIG. 3A. In other embodiments, a cavity is defined by the two or more walls of a sealable container as illustrated by the space inside the container in FIG. 3B. In some embodiments, the cavity has fixed size. In some embodiments, the cavity may change sizes.

In some embodiments, after the sealable container is sealed, the apparatus is configured to permit flow of the liquid portion of the liquid portion of the test sample from the one or more sealable containers through the at least one outlet port into the filtration filter and through the filtered outlet port when there is a pressure difference between the one or more sealable containers and the filtered outlet port.

Any pressure difference between the end of the filtered outlet port and the contents in the sealable container that causes the liquid portion of the test sample to flow out of the sealable container through the outlet port and into the filters will suffice. In certain embodiments, the pressure difference between the one or more sealable containers and the filtered outlet port is equal to or greater than about 4 pounds per square inch (psi). In some embodiments, the pressure difference between the one or more sealable containers and the filtered outlet port is from about 4 psi to about 10 psi. In some embodiments, the pressure difference between the one or more sealable containers and the filtered outlet port is from about 10 psi to about 15 psi. In some embodiments, the pressure difference between the one or more sealable containers and the filtered outlet port is from about 15 psi to about 20 psi. In some embodiments, the pressure difference between the one or more sealable containers and the filtered outlet port is from about 20 psi to about 30 psi. In other embodiments, the pressure difference between the one or more sealable containers and the filtered outlet port is equal to or greater than about 20 psi. In other embodiments, the pressure difference between the one or more sealable containers and the filtered outlet port is equal to or greater than about 30 psi. In other embodiments, the pressure difference between the one or more sealable containers and the filtered outlet port is equal to or greater than about 40 psi. In some embodiments, the higher the pressure is, the faster the test sample can pass through the apparatus.

In some embodiments, the apparatus comprises at least one filtration filter and at least one concentration filter. In some embodiments, the apparatus comprises one filtration filter and one concentration filter. However, it is envisioned that the number of filtration filters and/or concentration filters can vary depending on the specific application of the apparatus provided herein. For example, if the test sample is substantially free from particles in suspension, no filtration filter or only one filtration filter is needed. In other instances, if the test sample comprises large amount of particles, two or more filtration filters may be needed. Thus, an apparatus comprising only one filter is also encompassed by the present invention. Thus, in some embodiments, the apparatus does not comprise any filtration filter. In some specific embodiments, the apparatus of the present invention comprises only one filter, and the one filter serves as a concentration filter. In other embodiments, the apparatus comprises two or more filtration filters and at least one concentration filter. In a specific embodiment, the apparatus comprises two filtration filters and one concentration filter. A skilled person can determine how many filtration filters are needed based on the specific application. In the embodiments where one or more filtration filters are included, the liquid portion of the sample will contact the filtration filter first and contact the concentration filter subsequently, once the liquid starts to flow through the device.

As used herein, the term "filter" refers to any type of porous article or mass through which a gas or liquid can be passed to remove or trap from the liquid or gas. In some embodiments, the filters used herein utilize pores of various sizes or different thicknesses for filtration.

As contemplated by the present invention, the filters have pores with sizes bigger than the average size of a target microbe that is in or is suspected of being in the starting sample material, for example, a bacterium. As a unique and unexpected feature of the present invention, filters with bigger pore sizes are used. In some embodiments, the at least one filtration filter and at least one concentration filter independently have a pore size in the range of about 0.1 µm to about 40 µm. The pore sizes of the filtration filter and the concentration filter are not necessarily related to one another and are not necessarily tied to one another. In general, the pore size of the filtration filter will be larger than the pore size of the concentration filter. In specific embodiments, the pore sizes of the filtration filter is larger than the pore size of the concentration filter, and the pore sizes of the filtration filter(s) and the concentration filter(s) are all larger than the average size of the target microbe. In some embodiments, the at least one filtration filter and at least one concentration filter independently have a pore size in the range of about 0.5 µm to about 30 µm. In some embodiments, the at least one filtration filter and at least one concentration filter independently have a pore size in the range of about 1 µm to about 20 µm. In some embodiments, the at least one filtration filter and at least one concentration filter independently have a pore size equal to or greater than about 0.5 µm. In some embodiments, the at least one filtration filter and at least one concentration filter independently have a pore size equal to or greater than about 1 µm. In other embodiments of the present invention, the at least one filtration filter and at least one concentration filter independently have a pore size equal to or greater than about 2, 3, 4, 5, 6, 7, 8, 9, or 10 µm. However, filters with a pore size equal to or greater than about 20 µm are also encompassed by the present invention. For example, in some embodiments of the present invention, the at least one filtration filter and at least one concentration filter independently have a pore size equal to or greater than about 50 µm. The at least one filtration filter and at least one concentration filter can independently have the same pore size or different pore sizes.

In some embodiments, the at least one filtration filter and at least one concentration filter are membrane filters. As used herein, membrane filters or "membranes" refer to a thin, flat, selective barrier well-known in the art and which allows some components of a mixture to pass through but while preventing other components, based on size, shape, electrical charge, polarity or other physical characteristic. Such components that selectively pass through include but are not limited to molecules, ions, small or large particles, proteins, nucleic acids, microbes, etc. A membrane can be of animal or biological origin, or synthetic. The degree of selectivity of a membrane depends on the characteristics of the membrane and the component mixture that is passing through the membrane. For example, if components of the mixture are being separated based on size, the selectivity of the membrane will depend on the membrane pore size. Membranes can also be of various thickness, with homogeneous or heterogeneous structure. Membranes can be neutral or charged, and component passage through the membrane can be active or passive. Based on the physical characteristics of the membrane, one or more physical processes will affect or facilitate filtration. For example, pressure, electrical charge, concentration and the like can facilitate filtration according to the methods of the present invention.

In some embodiments, the at least one filtration filter and at least one concentration filter are hydrophilic or hydrophobic. The at least one filtration filter and at least one concentration filter can independently be made of a material such as, without being limited to, nylon, glass fiber, polyethersulfone (PES), polyvinylidene fluoride or polyvinylidene difluoride (PVDF), polytetrafluoroethylene (PTFE) hydrophilic, PTFE Hydrophobic, cellulose, cellulose acetate (CA), Mixed Cellulose Ester (MCE), polycarbonate, Polycarbonate Track Etch (PCTE), Polypropylene, Polyester track etched, or a material having a micro-structure substantially similar to any of the forgoing materials. In some embodiments, the at least one filtration filter and at least one concentration filter are independently made of a material selected from a listing comprising: cellulose, glass fiber, Mixed Cellulose Ester (MCE), nylon, polycarbonate, Polycarbonate Track Etch (PCTE), polyethersulfone (PES), polytetrafluoroethylene (PTFE) hydrophilic, polyvinylidene fluoride or polyvinylidene difluoride (PVDF), polycarbonate, or a material having a micro-structure substantially similar to any of the forgoing materials. A person skilled in the art would understand the micro-structure of a particular material.

In some embodiments, the at least one filtration filter and at least one concentration filter are made of the same materials. In other embodiments, the at least one filtration filter and at least one concentration filter are made of different materials. In a specific embodiment, the at least one filtration filter and the at least one concentration filter are PVDF filters, and either the filtration filter or the concentration filter has a pore size of 5 µm. In a specific test performed in connection with the present invention, test samples comprising *Salmonella* and *E. coli* were used. Although the diameters of *Salmonella* and *E. coli* are between 0.6 to 1 µm, unexpectedly, the microbes were trapped by the PVDF membrane filter having a pore size of 5 µm without the filter being clogged. This is surprising because one skilled in the art would have expected the microbes to pass through filter pores that are bigger than the diameters of the microbes.

In some embodiments, the at least one filtration filter comprises nylon and the at least one concentration filter comprises PVDF. In one specific embodiment, the at least one filtration filter comprises nylon and has a pore size equal to or greater than about 0.5 µm, and wherein the at least one concentration filter comprises PVDF and has a pore size in the range of about 0.5 µm to about 50 µm. In another specific embodiment, the at least one filtration filter comprises nylon and has a pore size equal to or greater than about 5 µm, and wherein the at least one concentration filter comprises PVDF and has a pore size in the range of about 1 µm to about 50 µm. In yet another specific embodiment, the at least one filtration filter comprises nylon and has a pore size of about 10 µm, and wherein the at least one concentration filter comprises PVDF and has a pore size of about 5 µm.

Figure 2A:
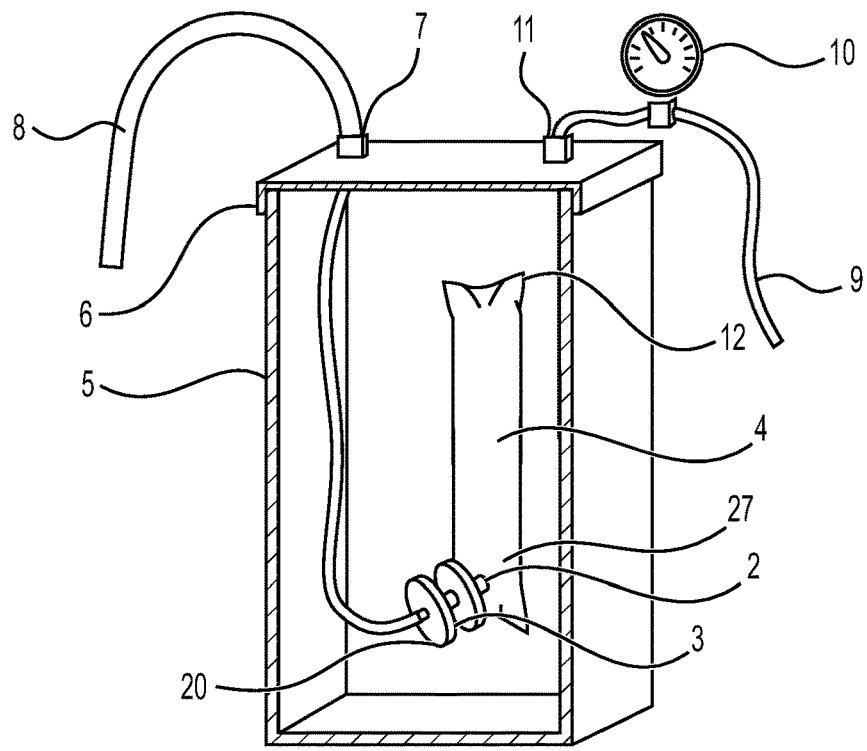
FIGS. 2A-2B show exemplary embodiments in which one or more flexible containers 4 with test samples are housed within a pressured chamber 5.

The apparatus of the present invention may further comprise at least one valve. As used herein, a "valve" refers to a device for controlling the flow of fluid, gas, or air through one or more channels, openings, or passageways by a movable part. In some embodiment, the valve has an automatic movable part that permits the passage of fluid, gas, or air through the channels, openings, or passageways. In some embodiment, the valve allows the movement of the fluid, gas, or air in one direction only. In such an embodiment, the valve is called a one-way valve. In some embodiments, the apparatus comprises a one-way valve located between the at least one filtration filter and at least one concentration filter. In certain embodiments, the one-way valve is configured to permit flow of the liquid portion of the test sample from the at least one filtration filter to the at least one concentration filter. For example, in an embodiment where the apparatus comprises one filtration filter and one concentration filter, the one-way valve is located between the filtration filter and the concentration filter, and is configured to permit flow of the liquid portion of the test sample from the one filtration filter to the one concentration filter. In other embodiments where the apparatus comprises a series of more than one filtration filters and one concentration filter. In such an embodiment, the one-way valve is located between the last filtration filter in the series and the concentration filter, and is configured to permit flow of the liquid portion of the test sample from the series of more than one filtration filters to the concentration filter. In a specific embodiment, the apparatus comprises two filters: one filtration filter 2 and one concentration filter 3, as shown in FIG. 2A, and the one-way valve is located between 2 and 3, and is configured to permit flow of the liquid portion of the test sample from the filtration filter 2 to the concentration filter 3.

In certain embodiments, the apparatus provided herein further comprises one or more inlets. In certain embodiment, a test sample comprising a liquid portion can flow in through an inlet as needed. In other embodiments, pressurized air or liquid can flow in through an inlet as needed. Examples of inlets are provided as 11 in FIGS. 2A and 2B, or 11 in FIG. 3E. Another example of inlets is provided as 16 in FIG. 3C.

Figure 2B:
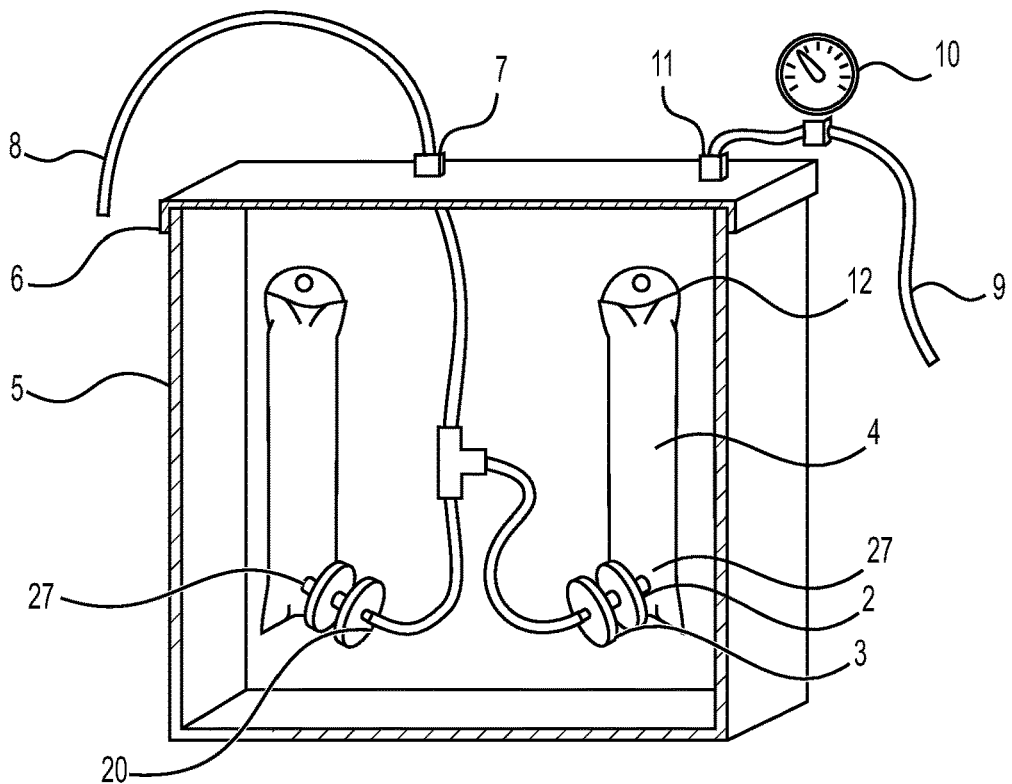

In some embodiments, the apparatus comprises at least one outlet port. The term "outlet port" as used herein refers to an opening through which a test sample comprising a liquid portion can flow. In some embodiments of the present invention, the at least one outlet port is located on the same side of the at least one filtration filter and at least one concentration filter. Such an embodiment is depicted as 27 in FIGS. 2A and 2B, between the sealable container 4 and the filtration filter 2. In other embodiments, the at least one outlet port is located between the at least one filtration filter and at least one concentration filter. Such an embodiment is depicted in FIG. 3C as indicated by the two stoppable or pluggable openings labeled 19. In this exemplary embodiment, the two openings labeled 19 are located between the filtration filter 2 and the concentration filter 3. A sample with concentrated microbes can be drawn from the concentration filter 3 as depicted in FIG. 3D.

In some embodiments, the apparatus provided herein comprises a filtered outlet port. To form a filtered outlet port, one or more filters can be connected to the at least one outlet port. In some embodiments, at least one filtration filter and at least one concentration filter are connected in sequence to the at least one outlet port to form a filtered outlet port. In some embodiments, one filtration filter and one concentration filter are connected in sequence to the at least one outlet port to form a filtered outlet port. In some embodiments, more than one filtration filter and one concentration filter are connected in sequence to the at least one outlet port to form a filtered outlet port. An example of a filter outlet port is provided as 20 in FIGS. 3C and 3D. Other examples of a filter outlet port are provided as 20 in FIGS. 2A, 2B, 3A 3B, 3E, 4B, and 5, as the opening through the outlet line 8 connected with the filtration filter 2 and the concentration filter 3.

In certain embodiments of the present invention, any number of the at least one of the filters, the inlets, the outlet ports, or the filtered outlet ports can be directly or indirectly connected to the one or more sealable containers. In other embodiments of the present invention, at least one of the filters, the inlets, the outlet ports, or the filtered outlet ports is directly or indirectly connected to the one or more sealable containers. In certain embodiments, all of the filters, the inlets, the outlet ports, or the filtered outlet ports are directly or indirectly connected to the one or more sealable containers. For instance, in certain specific embodiments, the apparatus comprises one filtration filter and one concentration filter, both of which are directly connected to the one or more sealable containers. Examples of such embodiments are provided in FIGS. 2A, 2B 3A, 3C-3E, 4B, and 5. In other specific embodiments, the apparatus comprises one filtration filter and one concentration filter and the two filters are indirectly connected to the one or more sealable containers. An example of such embodiments are provided in FIG. 3B. In some embodiments, the indirect connection comprises flexible tubing fluidly connecting the sealable container to any one or more of the filters, the inlets, or the outlets.

In some embodiments, the filtered outlet port comprises tubing, such that the terminal portion of the filtered outlet port can be extended. In other embodiments, the apparatus further comprises a collection vessel configured to receive at least a fraction of the liquid portion of the test sample after it passes through the filtered outlet port. In certain embodiments, the tubing of the filtered outlet port is fluidly connected to a collection vessel. Any container can be used as a collection vessel. In some embodiments, the collection vessel is a flexible container which permits the ambient pressure surrounding the collection vessel and the ambient pressure within the collection vessel to equilibrate. A skilled person can determine what a suitable collection vessel is according to the application.

The tubing used to extend the filtered outlet port can be flexible tubing. "Flexible tubing" as used herein can be a material in the form of a tube of any length, or a series or system of tubes of any lengths. The material of the tubing can be, but is not limited to, plastic, polyurethane, PVC, nylon, polyethylene, or ethylene propylene (FEP). In some embodiments, the tubing can be coiled or jacketed. In some embodiments, the tubing can be colored or non-colored. However, the present invention does not exclude any type of inflexible tubing. The material, length, or flexibility can be readily determined by a skilled person in the art. As used herein, fluidly connection means that the connection between or among any of the filters, the inlets, the outlet ports, or the filtered outlet ports to the sealable container permits the flow of a fluid into and/or out of one or more of the components of the apparatus, such as a fluid comprising the test sample.

In some embodiments, the apparatus is housed in a pressured chamber. In some embodiments, a portion of the apparatus is housed in a pressured chamber. For example, in certain specific embodiments, the one or more sealable containers or the at least one filtration filter and at least one concentration filter are housed in a pressured chamber. In other specific embodiments, the one or more sealable containers and the at least one filtration filter and at least one concentration filter are housed in a pressured chamber.

In some embodiments, the collection vessel is not housed in a pressurized chamber. In some embodiments, there is a pressure differential between the ambient pressure surrounding the sample container and the ambient pressure within the collection vessel that causes liquid to flow from the sample container, through the filtered outlet port and into the collection vessel. The sample container as used herein refers to the one or more sealable containers configured to receive a test sample. In some embodiments, the ambient pressure within the collection vessel is about atmospheric pressure.

As used herein, a pressured chamber or a pressure chamber, can be any type of chamber or container in which the pressure within the container can be increased to pressures above atmospheric pressures. Thus, the chamber can be made of any materials that fulfil this purpose. Such materials include, but are not limited to, wood, metals, polymers or plastics, glass, ceramics, biomaterials, composites, optical materials, metamaterials, or nanomaterials. In some embodiments, the pressured chamber can be connected to a pressure source. Non-exhausting examples of the pressure source can be a plunger, a piston, an impeller, a peristaltic pump, a pressurized vessel. A pressure vessel as used herein refers to a container designed to hold contents, such as gases or liquids, at a pressure substantially different from the ambient pressure. The appropriate pressure source for the pressure chamber can be determined and chosen by a person skilled in the art. An exemplary embodiment of a pressured chamber is depicted as 5 in FIGS. 2A and 2B. In some embodiments, the pressured chamber in connected to a pressure gauge. In some embodiments, a pressure gauge allows accurate control of the pressure inside the chamber.

In some embodiments, the one or more sealable containers is configured to allow a pressure source to be applied to the test sample. The pressure source can be, without being limited to, a plunger, a piston, an impeller, or a peristaltic pump. In one embodiment, the pressure source is a pressurized vessel.

The present invention also encompass apparatuses comprising two or more sealable containers. In some embodiments, the two or more sealable containers are fluidly connected in parallel. One exemplary embodiment is provided in FIG. 2B. In other embodiments, the two or more sealable containers are fluidly connected in tandem. In some embodiments, the two or more sealable containers are connected by patterned constrictions. In some embodiments, the constriction is a patterned constriction. In one embodiment, the patterned constriction is a labyrinth flow channel. In another embodiment, the patterned constriction is perforated. In yet another embodiment, the patterned constriction is dotted seals. In some embodiments, the patterned constrictions can prevent solid pieces of the test sample, for example, lettuce, from reaching the outlet. In some embodiments, the patterned constrictions function as coarse filters before the outlet. In some embodiments, the patterned constrictions between sealable containers creates resistance to flow between the two or more sealable containers. Exemplary embodiments are provided in FIGS. 4A and 4B.

The present invention further contemplates all variations of the embodiment that utilizes the same principle of patterned constrictions between the two or more sealable containers. In some embodiments, standoffs can be used to prevent the path for the liquid from sealing under pressure or being blocked. The two or more sealable containers can be used for various purposes, including but not limited to, allowing sequential introduction of different liquids or flowing additional clean liquid through the test sample, etc. The patterned constrictions can be used between any of the sealable containers.

In additional embodiments, the present invention provides methods of concentrating a microbe from a test sample comprising a liquid portion. In some embodiments, the methods comprise (1) passing the test sample through the apparatus provided herein, and (2) collecting a sample comprising the concentrated microbe from the concentration filter.

As used herein, the term "microbe" refers to any microorganisms, such as a bacteria, virus, fungi, or protozoa, cells, or other pathogens. Examples of microbes include infectious agents that may cause diseases or untoward or deleterious symptoms in an animal, such as human. As used herein, a microbe comprises bacteria, virus, fungi, and protozoa. The term "bacteria" is used herein to mean one or more viable bacteria existing or co-existing collectively in a test sample. The term may refer to a single bacterium (e.g., *Aeromonas hydrophilia, Aeromonas caviae, Aeromonas sobria, Streptococcus uberis, Enterococcus faecium, Enterococcus faecalis, Bacillus sphaericus, Pseudomonas fluorescens, Pseudomonas putida, Serratia liquefaciens, Lactococcus lactis, Xanthomonas maltophilia, Staphylococcus simulans, Staphylococcus hominis, Streptococcus constellatus, Streptococcus anginosus, Escherichia coli, Staphylococcus aureus, Mycobacterium fortuitum*, and *Klebsiella pneumonia*), a genus of bacteria (e.g., streptococci, *Pseudomonas* and enterococci), a number of related species of bacteria (e.g., coliforms), an even larger group of bacteria having a common characteristic (e.g., all gram-negative bacteria), a group of bacteria commonly found in a food product, an animal or human subject, or an environmental source, or a combination of two or more bacteria listed above.

In other embodiments, the term "microbe" also encompasses pathogens. The term "pathogen" as used herein refers to any microorganism that can cause disease. One exemplary embodiment of pathogen is foodborne pathogen that are present in the food and are the cause of major diseases, such as food poisoning. Exemplary of common foodborne pathogens include *Salmonella, E. coli* O157:H7, *E. coli* STEC, *Listeria, Campylobacter, Clostridium botulinum, Staphylococcus aureus, Shigella, Toxoplasma gondii, Vibrio vulnificus*, Norovirus, and *Legionella*.

In some embodiments, the collecting of the microbe from the concentration filter comprises counterflow elution of a liquid through the concentration filter. In some embodiments, the concentrated microbe can be collected from between the at least one filtration filter and at least one concentration filter. An exemplary embodiment is illustrated in FIG. 3D. In one embodiment, the apparatus comprises at least one filtration filter and at least one concentration filter, and the concentrated microbe is collected from the concentration filter after the test sample has passed through both filters. Examples of such embodiments are illustrated in FIGS. 2A-2B, where the concentrated microbe can be collected from the concentration filter 3.

To collect microbes from a filter, the invention may rely upon a common practice in the art includes introducing the filter into a tube or container with a suitable liquid, and sonicating or applying shear to it. Subsequently, the microbes are re-suspended in the liquid. The present invention, however, also can rely on a simplified and rapid microbe recovery and collection method by counterflow elution of a liquid through the concentration filter. In a specific embodiment, after the test sample comprising a liquid portion has passed through the filters, the concentration filter is disassembled from the apparatus. An appropriate volume of liquid, such as water or a buffered solution, is pumped backwards, in the direction opposite to the filtration direction used previously. This is an example of the "counterflow elution" proposed by the present invention. In one embodiment, the liquid portion of the sample is the same as the liquid used in the elution and collection of the microbe.

In some embodiments, about 1-10 ml of deionized water is pumped backwards. In other embodiments, about 1-5 ml of deionized water is pumped backwards. The volume of the liquid can be adjusted based on various factors, for example, the size of the membrane filter. In one exemplary embodiment, about 1.5 ml of deionized water is pumped backwards to collect the concentrated microbe from a membrane filter of about 25 mm in diameter. In other embodiments, the liquid can be, but is not limited to culture medium, a buffered solution, and/or mixtures thereof. The concentrated microbe can be collected from the liquid. The volume of the liquid and the type of the liquid can be determined by a skilled person according to the application.

In some embodiments, the method further comprises recovering the microbe from the sample comprising the concentrated microbe. In some embodiments, the method of the present invention also encompasses processing a sample comprising the concentrated microbe. In one embodiment, the sample comprising the concentrated microbe is introduced into a vial or tube. Any type of vial or tube can be used to collect the sample. In another embodiment, the collected sample comprising the concentrated microbe is centrifuged. In some embodiments, the speed of centrifugation is between about 10 G to about 100 G. In one embodiment, the speed of centrifugation is about 50 G. In one embodiment, the speed of centrifugation is about 22 G. In one embodiment, the speed of centrifugation is greater than about 100 G. In one embodiment, the speed of centrifugation is less than about 10 G. In one embodiment, the supernatant from the centrifugation is discarded. In a further embodiment, a pellet from the centrifugation is collected and is the final concentrate. In certain embodiments, the recovering can be achieved by plating the processed sample comprising the concentrated microbe on selective media.

In some embodiments, the method further comprises detecting the microbe from the processed sample comprising the concentrated microbe. In certain embodiments, the detecting can be achieved by molecular methods such as selectively culturing the microbe or by polymerase chain reaction (PCR). In certain embodiments, the detecting can be done by a real-time PCR (RT-PCR). In certain embodiments, the detecting can be done by a quantitative real-time PCR (qRT-PCR). In certain embodiments, the detecting can be done by a quantitative PCR (qPCR). In other embodiments, the processed sample comprising the concentrated microbe may be assayed for contamination by any other PCR-based detection techniques not listed here. In another embodiment, the processed sample comprising the concentrated microbe may be assayed by plating on selective media for specific microbes.

Following the methods for separating microbe from a test sample provided herein, the collected and/or recovered sample containing the microbe can be further processed or preserved by techniques commonly used in the art, including but not limited to, dilution, concentration, freezing, freeze-drying or lyophilization, cryopreservation, hypothermic preservation, and vitrification.

The methods may be used to detect the presence of any cellular contaminant or microbe where the maintenance of cellular viability is important in the sample preparation process. In one embodiment, the present disclosure provides methods for separating microbe from a test sample. In certain embodiments, the methods generally comprise extracting the microbe from the test sample by processing the sample in the apparatus provided herein. The term "colony forming unit" (CFU) is a unit commonly used in microbiology to estimate the number of viable microbe cells in a sample. Viable is defined as the ability to multiply under controlled conditions. Counting CFU requires culturing the microbes and counts only viable cells. As used herein, the term CFU means the unit of live microbe capable of forming a colony in a plate.

In additional embodiments, the method of the present invention further comprises preparing a test sample for passing through the apparatus. In some embodiments, the preparation encompasses cutting, chopping, dicing, mincing, grounding, heating, cooling, freezing, mixing, or filtering the test sample. In one embodiment, the preparation comprises mixing the sample with a flow liquid. In some embodiments, the preparation can be facilitated by adding a surfactant to the flow liquid or the test sample. Exemplary surfactants include, but are not limited to, TWEEN or polyethylene glycol (PEG). In one embodiment, the surfactant is 1% TWEEN. The optimal concentration of the surfactants can be determined by one skilled in the art. In certain embodiment, the surfactant is to aid in removing microbe from the sample surface. In certain embodiments, the extraction can be enhanced by preventing microbe from attaching to new surfaces, such as the membrane filter surface.

A further embodiment of the present invention provides a dynamic microbe concentrator. In some embodiments, the concentrator comprises (a) a filter located above a disk, (b) one cavity between the filter and the disk, (c) one or more inlets and at least one outlet connected directly to the cavity between the disk and the filter, and (d) at least one additional outlet on the side of the filter away from the disk. In some embodiments, the microbe concentrator is referred to as a dynamic microbe concentrator.

In some embodiments of the microbe concentrator device, the filter is a membrane filter as provided herein. In certain embodiments, the membrane filter is a microfiltration membrane. As used herein the term "microfiltration refers to a type of physical filtration process where a contaminated fluid is passed through a special pore-sized membrane to separate microorganisms and suspended particles from a test sample. In some embodiments, the microfiltration membranes have a pore size within the range of about 0.1 µm to about 40 µm. In some embodiments, the microfiltration membranes have a pore size within the range of about 0.45 µm to about 40 µm. In some embodiments, the microfiltration membranes have a pore size within the range of about 1 µm to about 30 µm. In some embodiments, the microfiltration membranes have a pore size within the range of about 2 µm to about 20 µm. In some embodiments, the microfiltration membranes have a pore size within the range of about 10 µm. In one embodiment, the microfiltration membrane has a pore size of about 5 µm. In some embodiments, the microfiltration membranes have a pore size within the range of about 3 µm.

In some embodiments of the concentrator provided herein, the membrane filter supports the flow through of the test sample and holds the microbe from the test sample. The membrane filter can be any filter encompassed in the present invention. In one exemplary embodiment, the membrane filter of the concentrator comprises PES. In another exemplary embodiment, the membrane filter of the concentrator comprises polycarbonate. The pore size of the membrane filter may be between about 0.4 µm to about 3 µm. In certain embodiments, the membrane filter has a pore size of about 0.5, about 0.6, about 0.7, about 0.8, about 0.9, about 1.0, about 1.2, about 1.3, about 1.4, about 1.5, about 1.6, about 1.8, about 1.9, about 2.0, about 2.2, about 2.4, about 2.6, about 2.8, or about 3.0 µm. In certain embodiments, the membrane filter has a pore size of 1.2 µm.

In some embodiments, the disk of the concentrator has vanes. In other embodiments, the disk has magnets or other ferromagnetic materials so that the disk can be actuated externally by magnetic coupling.

In certain aspects of the present invention, the concentrator can be used in connection with a Microfiltration Assisted Counter flow Elutriation (MACE) separator. A MACE separator is disclosed in the international application No. PCT/US19/49717, which is incorporated herein by reference in its entirety. In one embodiment, the concentrator is used after the MACE separator. In another embodiment, the extract from a MACE separator is treated with digestive enzymes and a surfactant, such as TWEEN 20, prior to its introduction into the concentrator.

In one embodiment, a test sample comprising a liquid portion is introduced into the concentrator directly into the cavity between the disk and the membrane filter, flowed past the membrane filter and out of the concentrator through an outlet. Next, a relatively large volume of water or other liquid may be introduced into the cavity between the disk and membrane filter past the filter to rinse out molecules in suspension. In some embodiments, the volume of the water or other liquid is between about 100 ml to about 500 ml. In an exemplary embodiment, the volume of the water or other liquid is about 300 ml. In certain embodiments, the water or other liquid is sterile. Subsequently, the disk is rotated at a rotation speed from about 60 rpm (revolutions per minute) to about 3000 rpm. In one exemplary embodiment, the disk is rotated at a rotation speed of about 400 rpm. The rotation of the disk is performed for about 5 seconds to about 1 min. In one exemplary embodiment, the disk is rotated for about 10 seconds. In another exemplary embodiment, the disk is rotated for about 20, about 30, about 40, or about 50 seconds. In further embodiments, the rotating disk is stopped and the liquid between disk and membrane filter, i.e., the concentrate, is recovered through a second outlet at the cavity between the disk and the membrane filter. The concentrate is then introduced into a vial, centrifuged at an optimal speed. For example, in one embodiment, the concentrate in a vial is centrifuged at about 22 G. The optimal speed can be determined by a person of ordinary skill in the art. After the centrifugation, the supernatant can be discarded. The resulting pellet is the concentrated microbe that can be analyzed with any suitable molecular methods to detect specific microbes.

Although the detection of foodborne pathogens is an important application of the present disclosure, the method may, of course, also be applied to samples of other origin, including but not limited to, samples for clinical or environmental assays, such as blood, urine, or polluted water, etc.

Another advantage of the present invention is that the apparatuses and methods can be adapted to process multiple test samples simultaneously. In some embodiments, the apparatuses provided herein can be used to perform the separation and concentration of microbes from 1 to 100 samples simultaneously. In some embodiments, the apparatuses provided herein can be used to perform the separation and concentration of microbes from 50 samples simultaneously. In a specific embodiment, 20 samples can be processed simultaneously.

The method provided herein can be completed faster than alternative methods currently available. In one embodiment of the present invention, the method can be complete in less than about 5 minutes. In one embodiment, the method can be completed in less than about 10 minutes. In another embodiment, the method can be completed in less than about 30 minutes. In another embodiment, the method can be completed in less than about one hour. In another embodiment, the method can be completed in less than about four hours. In yet another embodiment, the method can be completed in less than about eight hours. However, the method can be completed in any duration of time beyond those recited here as needed.

The term "about" or "approximately" as used herein means within 20% of a given value or range, i.e., plus and minus 20% of a value. In a more specific embodiment "about" means within 10% of a given value or range, i.e., plus and minus 10% of a value. In a more specific embodiment "about" means within 5% of a given value or range, i.e., plus and minus 5% of a value. In an even more specific embodiment "about" means within 2% of a given value or range, i.e., plus and minus 2% of a value.

Unless defined otherwise, all technical and scientific terms used herein have the same meaning as commonly understood by one of ordinary skill in the art (e.g., in microbiology, cell culture, molecular genetics, nucleic acid chemistry, and biochemistry). Standard techniques are used for molecular, genetic, and biochemical methods.

II. Exemplary Devices

In certain embodiments of the present invention, apparatuses, devices, systems, and methods for rapid and efficient microbe separation, concentration, and from test samples are provided.

FIG. 1 is a flow chart demonstrating the basic concept of the apparatus and method of the present invention for separating, concentrating, and harvesting microbes from a test sample. Briefly, the liquid portion of the test sample 1 is pumped through a filtration filter 2, through a concentration filter 3, and to waste. Samples comprising concentrated microbes can be harvested from the concentration filter. The apparatus can have any number of filtration filters, such as 0, 1, 2, 3, 4, or more, and one concentration filter. In some embodiments, the liquid portion of the test sample starts to flow through the apparatus, it will contact the filtration filter first and then contact the concentration filter. The microbe concentrate can be collected from after or between any of the filters. In an exemplary embodiment, the apparatus comprises one filtration filter and one concentration filter, and the microbe concentrate can be collected from between the filtration filter and the concentration filter. In another exemplary embodiment, the microbe concentration can be collected from after the sample passes through the concentration filter. In some embodiments, the microbe concentration can be collected from the concentration filter. In another embodiment, the microbe concentration can be collected from the last concentration filter in the series of filters.

FIGS. 2A-2B show exemplary embodiments in which one or more containers 4 with test samples are housed within a pressured chamber 5. The one or more containers 4 can be any type of flexible receptacles, such as plastic bags or pouches. However, the container or containers 4 can also be rigid or inflexible. In one embodiment, the filtration filter 2 can be connected directly to the container 4. In another embodiment, the filtration filter 2 can be connected indirectly to the container 4 via flexible tubing. The opening in the container 4 connects to the filtration filter 2, and the connection forms an outlet port 27. In some embodiments, the outlet port 27 comprises flexible tubing. The filtration filter may allow some microbe to pass through. The at least one filtration filter and at least one concentration filter can be connected further down to the outlet line 8, inside or outside of the pressured chamber 5. The concentration filter 3 can trap the microbe and can be connected to the filtration filter 2. In some embodiments, the at least one filtration filter and at least one concentration filter are fluidly connected in sequence to the at least one outlet port to form a filtered outlet port 20. Once the liquid portion of a test sample starts to flow through the apparatus, the liquid will contact the filtration filter first and contact the concentration filter subsequently. Additional filters can be connected thereto consecutively. In some embodiments, the microbe sample can be collected from between the filtration filter 2 and the concentration filter 3. In other embodiments, the microbe sample can be collected after the concentration filter 3. In further embodiments, the microbe sample can be collected from between any of the filters or after the last filter in the chain. The lid 6 is sealed around the waste port 7, allowing the inside of the tube to be exposed to atmospheric pressure, while the inside of the chamber 5 is pressurized at the inlet 11. In some embodiments, a pressure gauge 10 and inlet tube 9 can be connected to a pressure source, such as a regulated air supply. Once the sample has been added to the container 4, it can be sealed, as shown in 12. In some embodiments, there is a minimal pressure differential between the container 4 and the inside of the pressured chamber 5, this seal does not need to be especially strong. In other embodiment, the pressure differential between the container 4 and the inside of the pressured chamber 5 can be large, and thus this seal needs to be strong enough to withstand the pressure differential. In some embodiments, after the one or more sealable containers is sealed, the liquid portion of the test sample flows from the one or more sealable containers through the at least one outlet port 27 into and through the filtered outlet port 20 when a pressure difference is applied to the test sample.

Figure 3A:
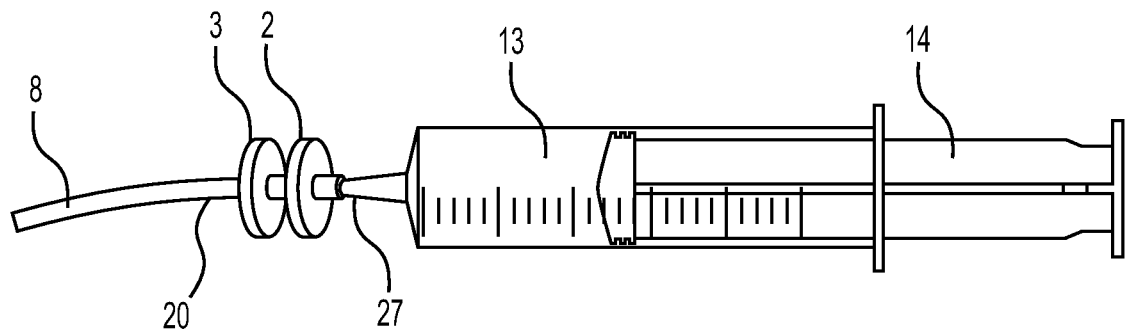
FIG. 3A shows an embodiment of a syringe impelled version of the device.

In another embodiment of the invention, the device can be syringe impelled, as shown in FIG. 3A. In one specific embodiment, the sample is placed inside the cylinder body of a syringe 13. The syringe 13 can be directly connected to one or more filters, as depicted by filters 2 and 3. In an exemplary embodiment, the filtration filter 2 and the concentration filter 3 are attached to the nozzle of the syringe and an outlet tube 8, as shown in FIG. 3A. The pressure differential across membrane filters is achieved by operating the syringe plunger 14. Using a rigid container with a variable volume, such as a syringe, ensures a high percentage of the liquid is captured because the sample is compressed by the plunger. This embodiment can be operated by hand with no additional apparatus for control, and a relatively high pressure can be achieved without a significant risk of bursting. Because the volume is changed directly, this device can be controlled not only at a constant pressure, but also at a constant volumetric flow rate if the application requires it. In one embodiment, a standard syringe pump could be used to operate the syringe at a constant flow rate.

Figure 3B:
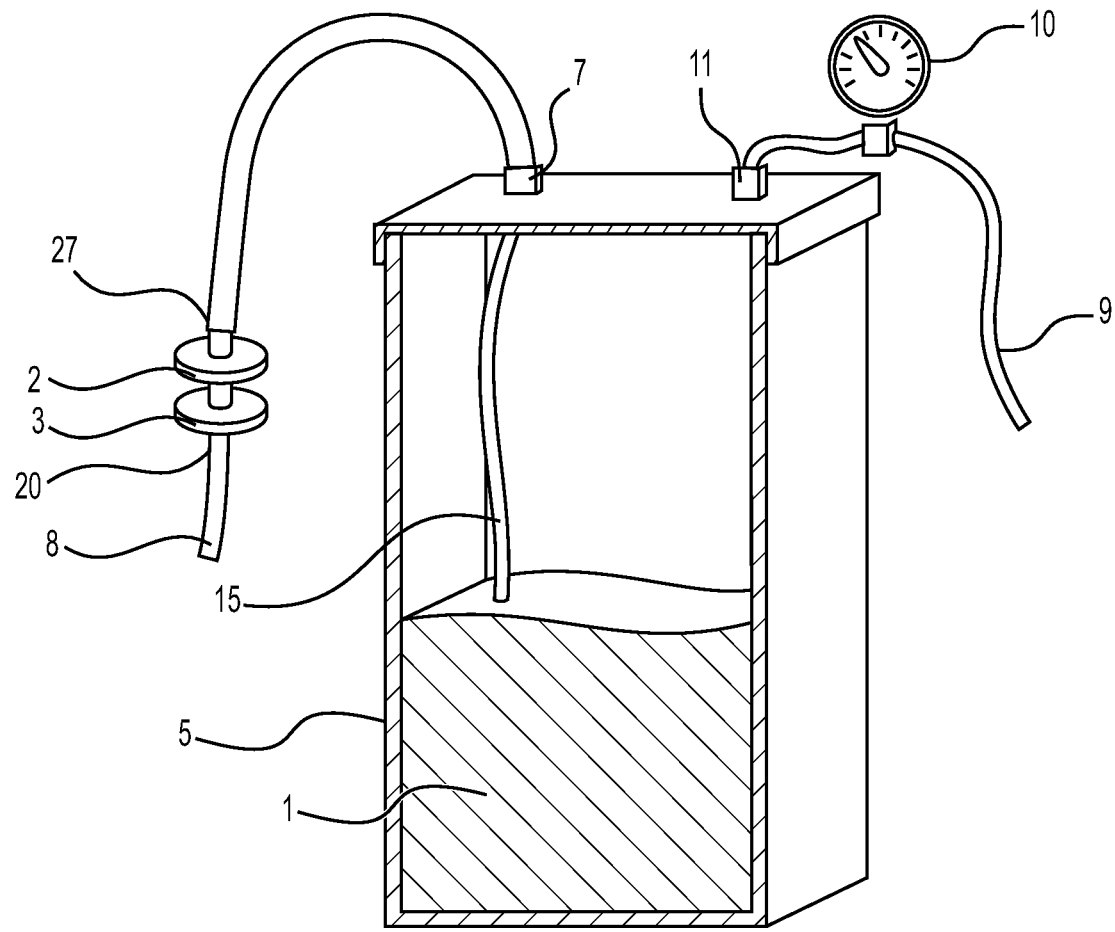
FIG. 3B shows that a pressurized chamber 5 functions as the sample container.
Figure 3C:
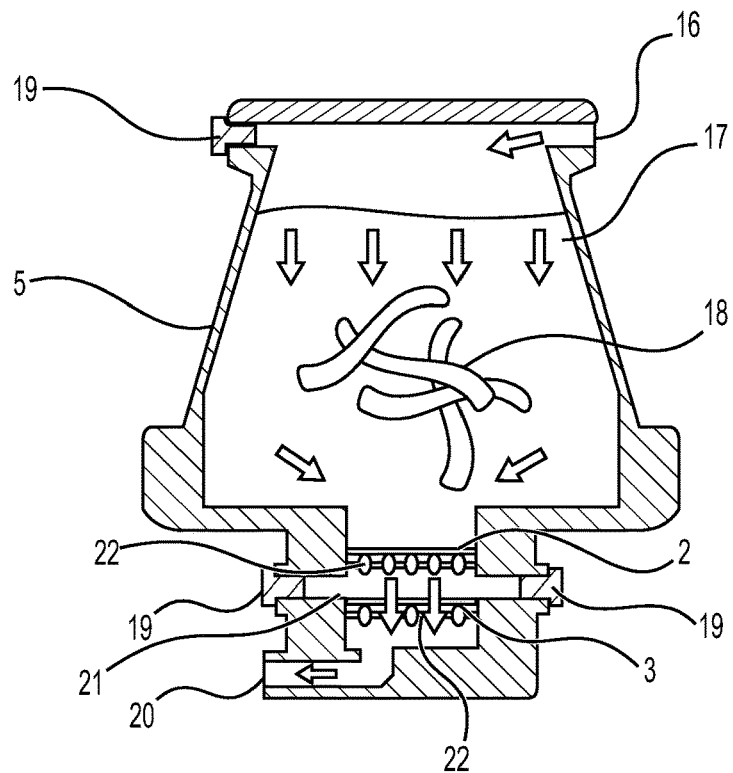
FIGS. 3C-3D both depict a version of the pressurized rigid container embodiment.
Figure 3D:
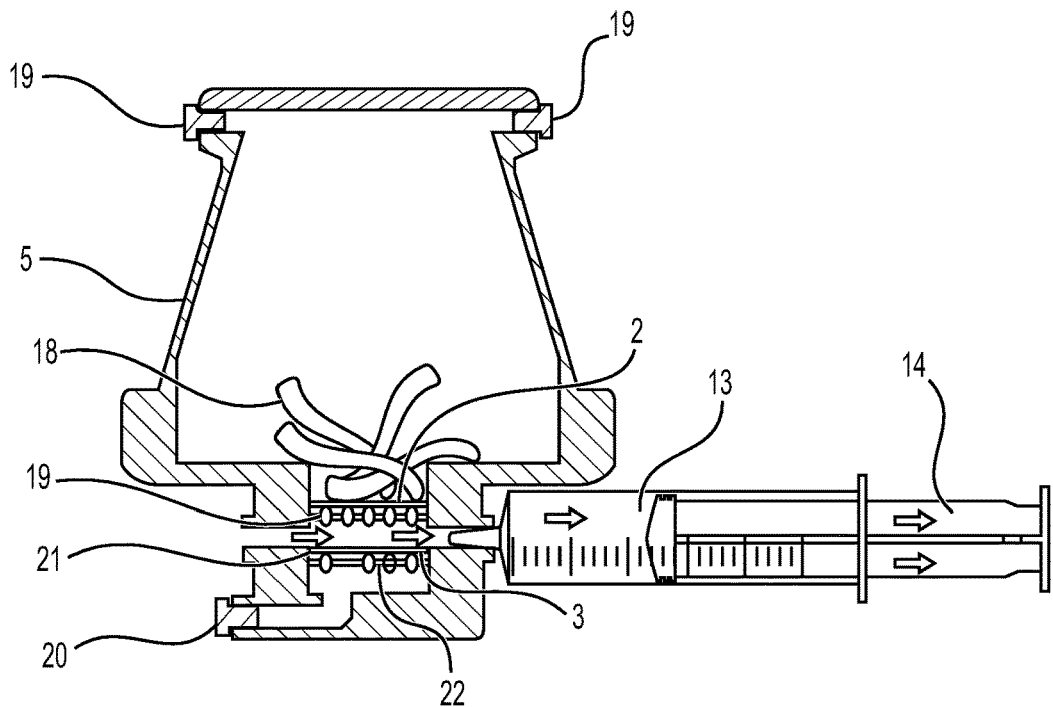

In one embodiment, the pressurized chamber 5 shown in FIG. 3B also functions as the sample container. The inside of the sample container is pressurized to pass the liquid media 1 mixed with the sample through the waste tube 8, and through the filtration filter 2 and concentration filter 3. In some embodiments, the liquid media 1 is the flow liquid provided herein.

A rigid container as shown in the embodiment in FIG. 3B is capable of withstanding higher pressures. In addition, a rigid container does not change volume substantially depending on pressure. Thus, the form of the sample will not impact how effectively the liquid media can be extracted.

In other embodiments of the present invention, one or more containers with intermediate flexibility can be used. In one specific embodiment, the one or more containers with intermediate flexibility filled with a flow liquid can positioned between the pressure source and an inlet, such as 9 in FIG. 3B, of this device to expose the sample to additional flow liquid. In one embodiment, the one or more containers with intermediate flexibility can be used to pass clean flow liquid across the sample to increase collection efficiency, to purify the sample, or to add chemicals in a particular order to the sample to improve the results or reliability.

In some embodiments, the one or more containers can be pressurized rigid containers as shown in FIGS. 3C-3D. In one embodiment, the rigid container 5 is modeled in a specific shape and configuration. One specific embodiment is shown in FIG. 3C. In this particular embodiment, pressurized air or liquid is passed into the inlet 16, forcing the liquid 17 comprising the test sample into the chamber downwards and through one or more filters, such as the filtration filter 2 and concentration filter 3 in FIG. 3C. Additional filters may be added. The filtered waste flows out the filtered outlet port 20. The device may contain additional openings and can be plugged when not in use, such as 19 in FIG. 3C. The filtration filter 2 blocks the test sample 18. The at least one filtration filter and at least one concentration filter, such as 2 or 3, respectively, can be backed by a mesh support structure 22 that prevents the filter from puncturing or bursting when a pressure differential is created. The mesh support structure can be any structure that can fulfill this purpose. Exemplary mesh support structures include, without limiting to, sieving screens generally comprise a wire mesh of openings, holes, or gaps, with specified or varied sizes, to separate a test sample containing particles or microbes into different groups based on their sizes. A person skilled in the art would contemplate various shapes and configurations based on the particular application of the device.

In one embodiment, a syringe 13 can be used to collect the concentrate when the filtration is completed, as depicted in FIG. 3D. In a specific embodiment, one of the plugs 19 sealing the collection chamber 21 is removed and the syringe plunger 14 is extended to pull the sample comprising the concentrated microbe from the chamber.

Certain embodiments of this invention can be completely assembled from off-the-shelf parts. One embodiment of the present invention can be a single unit that includes the filters internally with ports to collect the final concentrated sample. In other embodiments, the parts can be connected with each other. In some embodiment, the parts can be connected by flexible tubing. One skilled in the art would readily contemplate various configurations of the device with the information provided herein.

In other embodiments, the sample container, such as the flexible container 4 depicted in FIG. 3E, is not enclosed in a pressurized chamber. In such embodiments, the container is pressurized directly through an air inlet 11. The filtration filter 2 and concentration filter 3 may attach directly to the sample container 4 at the waste port 7. Consequently, the filtered liquid can pass through the outlet tube 8. In this embodiment, any of the sealing portions in the device, including the flexible container 4, the air inlet 11, and the waste port 7, need to be strong enough to withhold the pressure differential between the inside of the sample container and the ambient environment. A pressure as low as 4 psi can be applied to the flexible container 4 in the embodiment depicted in FIG. 3E and can be sufficient to perform the present invention. However, higher pressures are also contemplated by the present invention. In further embodiments, any of the additions, such as those depicted in FIGS. 2A and 2B, can be added to the embodiment depicted in FIG. 3E.

Figure 4A:
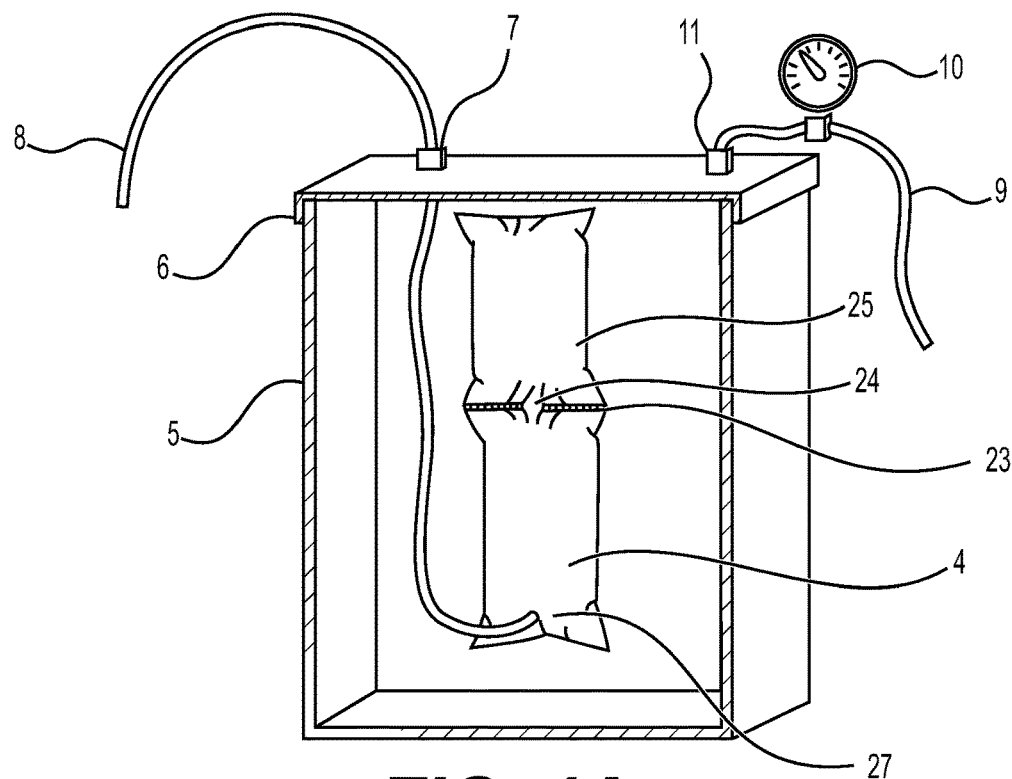
FIG. 4A depicts additions to the pressurized chamber 5 and flexible container 4 that improves the function.
Figure 4B:
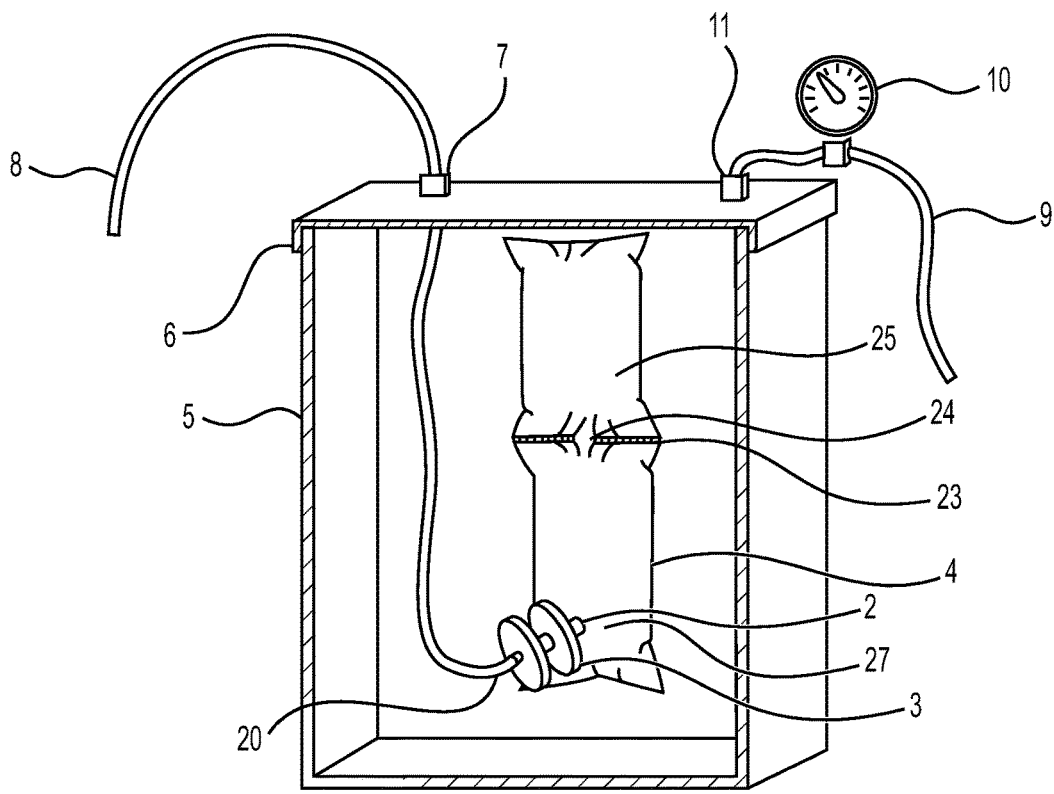
FIG. 4B shows an embodiment in which the flexible container is connected to the outlet tubing via two filters used to separate and concentrate microbes.

FIG. 4A depicts additions to the pressured chamber 5 and flexible container 4 that improve the function. In this specific embodiment, the pressurization of the chamber 5 creates a pressure difference directly between the liquid in the flexible container 4 and the ambient environment outside of the chamber 5 through the outlet tubing 8. The sample in the flexible container 4 in contact with the outlet tubing 8 is driven out through the tubing. In one embodiment, a compartment 25 is connected to the flexible container 4 through a constriction 23. The liquid in the compartment 25 further away from the outlet is also pressurized. The constriction 23 creates a resistance to flow from the compartment 25 to the flexible container 4. As a result, the effuse from compartment 25 is delayed and is smaller than the flexible container 4. FIG. 4B further shows an embodiment in which the flexible container 4 is connected to the outlet tubing via two filters. The filters can be used to separate and concentrate microbes. Any number of filters can be used according to the specific application of the device.

In some embodiments, the constriction 23 is a patterned constriction. Many variations of the embodiment are possible to utilize the same principle of patterned constrictions between the compartment 25 and the flexible container 4. In some embodiments, additional sealable containers can be added to the compartment 25, the flexible container 4, or both, thus creating a container comprising multiple sealable containers. Such additional sealable containers can be used for various purposes, including but not limited to, allowing sequential introduction of different liquids or flowing additional clean liquid through the test sample, etc. The patterned constrictions can be used between any of the sealable containers.

Figure 5:
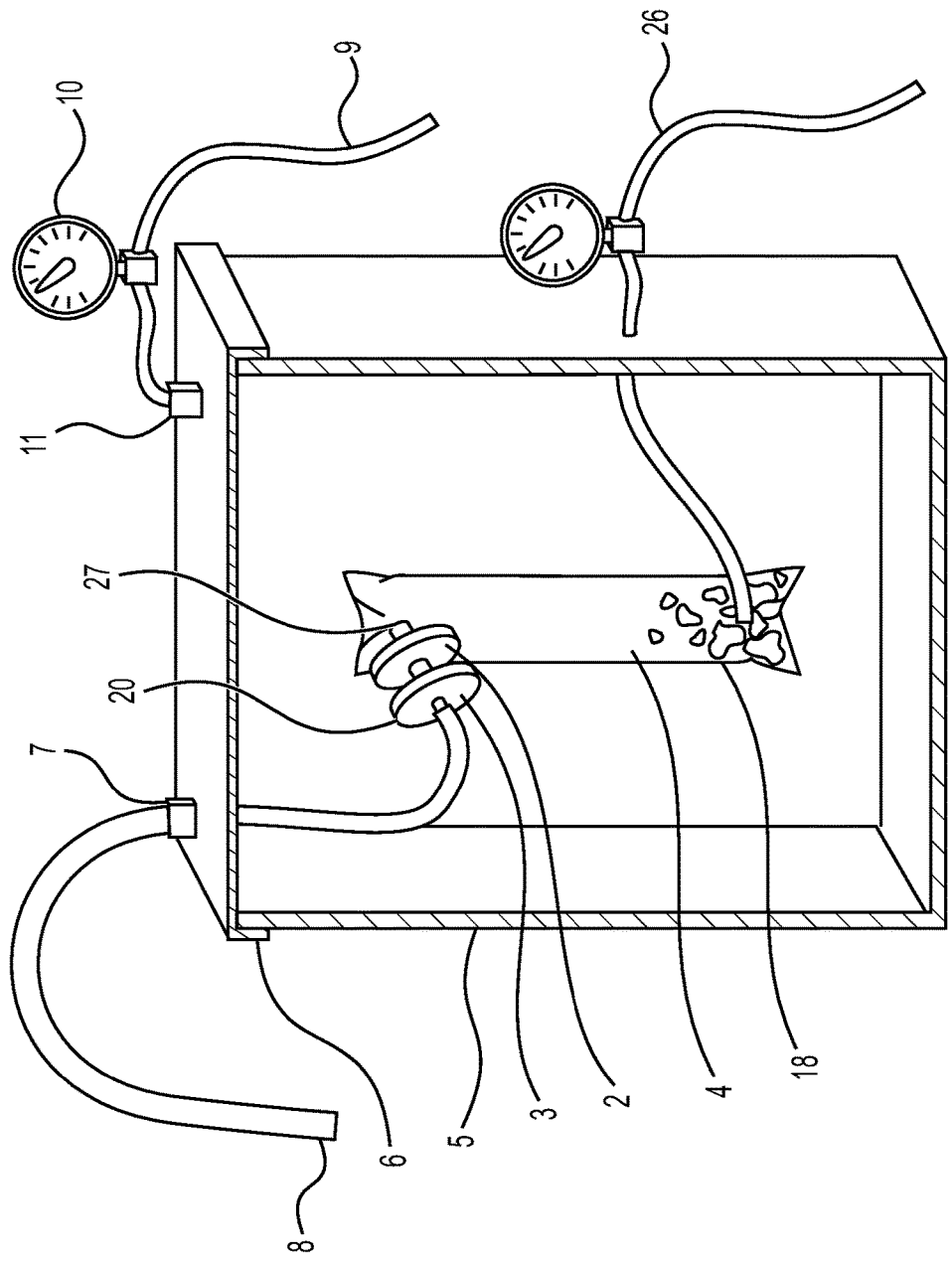
FIG. 5 shows an embodiment used to perform microfiltration assisted counterflow elutriation (MACE) separation on a flexible container.

FIG. 5 shows an exemplary embodiment that can be used to perform counterflow separation on a container 4. The container 4 here can be flexible or rigid. In a particular embodiment, the container is flexible. In this embodiment, the flexible container 4 has at least one inlet and one outlet. The inlet is positioned near the bottom of the flexible container 4 and the outlet is positioned near the top of the flexible container 4. In other embodiments, the inlets and the outlets can be positioned anywhere on the flexible container 4 as long as the device can be used for counterflow separation. A flow liquid can be introduced through the inlet 26 at a pressure higher than the pressure from the inlet tube 9 as indicated by the pressure gauge 10. The dual-pressure differential keeps the flexible container 4 positively pressurized during the process so that it maintains the volume constant while the flow liquid is flown counter to sedimentation. The flow rate can be established based on the difference of pressures between the flow liquid being pumped through 26 and the pressure at the outlet 8. Notably, such an embodiment is particularly advantageous if a higher pressure differential is required to establish a flow. In particular, the flexible container 4 does not burst open because it is only exposed to the pressure difference between the inlet 26 and the inlet tube 9. The pressure difference between the inlet 26 and the inlet tube 9 can be set to be constant and arbitrarily small, independent of the pressure difference between inlet 9, as indicated by gauge 10, and atmospheric pressure which drives the flow through the filter.

Figure 6:
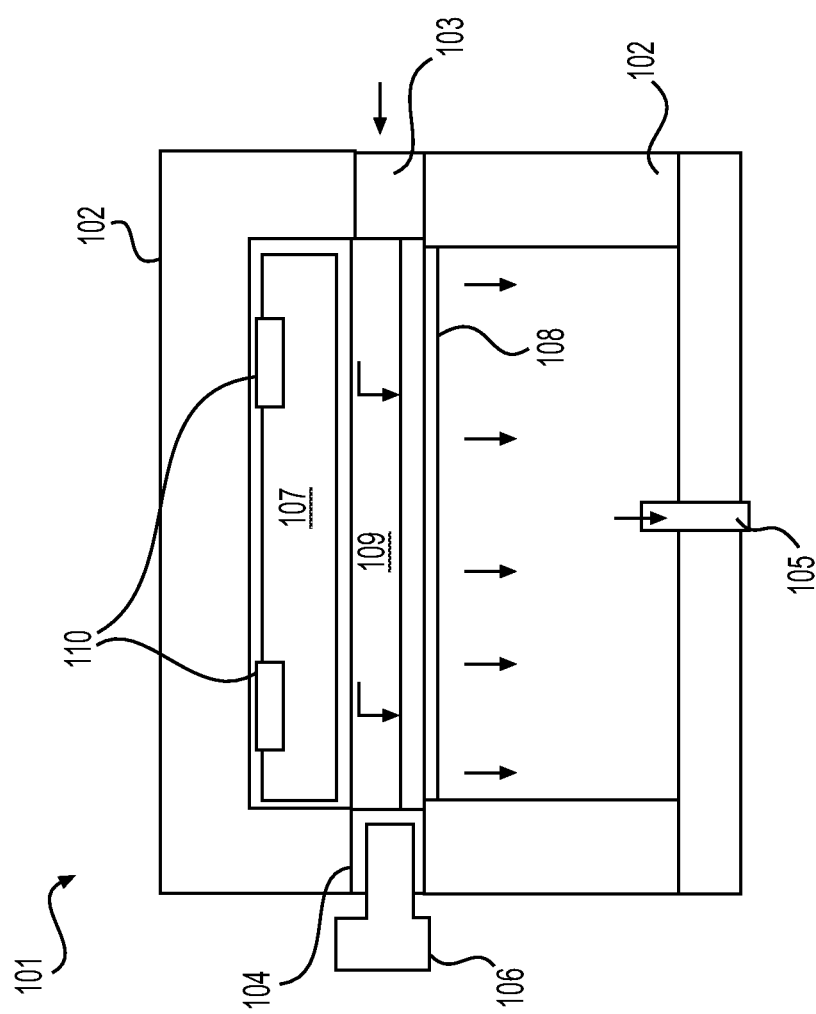
FIG. 6 shows an exemplary schematic illustration of a dynamic microbe concentrator.

In other embodiments of the present invention, a dynamic microbe concentrator for rapid and efficient microbe concentration and recovery from test samples are provided. FIG. 6 shows an exemplary illustration of a dynamic microbe concentrator. The dynamic microbe concentrator 101 comprises a plastic housing 102, in inlet 103 and two outlets, 104 and 105. Initially one of the outlets is closed with a plug 106. The dynamic microbe concentrator's inside is comprised by a membrane filter 108, a disk 107, and a cavity 109 between disk and membrane filter. The disk may have magnets 110 or magnetic materials so that it can be actuated with an external magnetic field via magnetic coupling. The housing's material may be plastic, paper etc.

Figure 7A:
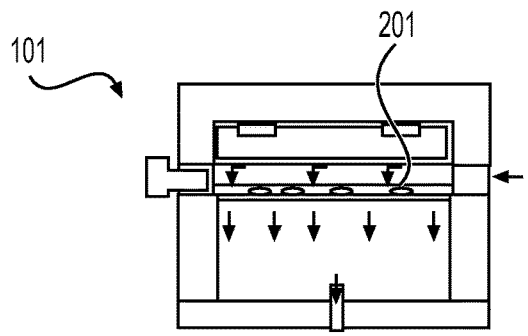
FIGS. 7A-7C show an exemplary method of operation of dynamic concentration.
Figure 7B:
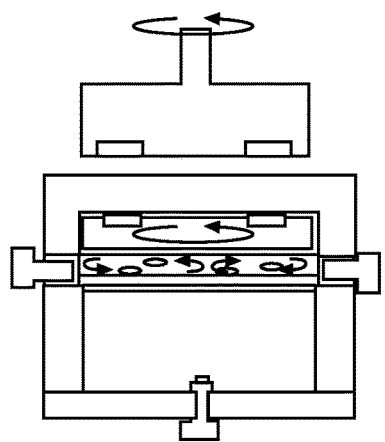
Figure 7C:
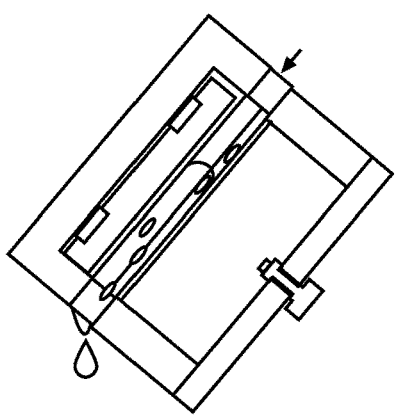

FIGS. 7A-7C show an exemplary method of operation of dynamic concentration. In FIG. 7A, liquid containing microbe is introduced through inlet 103. The liquid enters cavity 109 and flows past the membrane filter 108 and out of the dynamic filter through outlet 105. Solids such as microbe are retained at the membrane filter's surface in a dead-end microfiltration fashion. In FIG. 7B inlet 103 and outlet 105 are plugged and the disk is made to rotate via magnetic coupling with an external rotor. The rotation of the disk creates shear on the membrane filter's surface facing cavity 109, desorbing the microbe from said surface. In FIG. 7C, the plugs in inlet 103 and outlet 102 are removed, and the liquid in cavity 109 is recovered either using gravity or by introducing air or gas through one of the openings. The exemplary method presented in FIGS. 7A-7C is a simplified version of the operation of the dynamic concentration. In some embodiments, the method may include additional steps such as flowing sterile prefiltered liquid after the dead-end filtration to remove molecules in the liquid in cavity 109.

FIGS. 8A and 8B show a photograph and a schematic diagram of an exemplary dynamic microbe concentrator, respectively. Particularly, FIG. 8A shows a photograph of an exemplary dynamic microbe concentrator (301) having one inlet 302, and two outlets 303 and 307. FIG. 8B shows a schematic cross section an exemplary dynamic microbe concentrator. The dynamic microbe concentrator comprises one inlet 302, an outlet 303, and an opening 307, a rotating disk 304, a membrane filter 305, and a supporting structure for the membrane filter 306.

FIG. 9A shows a photograph of the exemplary dynamic concentration comprised of two parts (408 and 409) (FIG. 9B) that can be disassembled to clean and reassembled for use.

FIG. 10A shows a close-up photograph of the assembly 408. The assembly 408 comprises a membrane filter 505 and a supporting structure 506. FIGS. 10A-10F shows different views and schematics of the different parts comprising the upper part of the dynamic microbe concentrator.

Figure 11A:
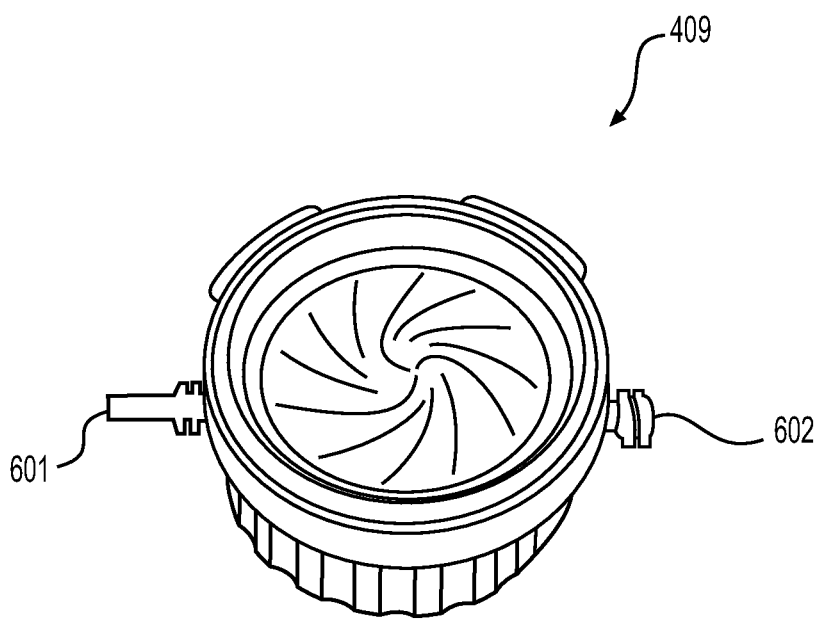
FIGS. 11A and 11B show exemplary second half of an embodiment of the dynamic microbe concentrator, having a shear producing rotor.
Figure 11B:
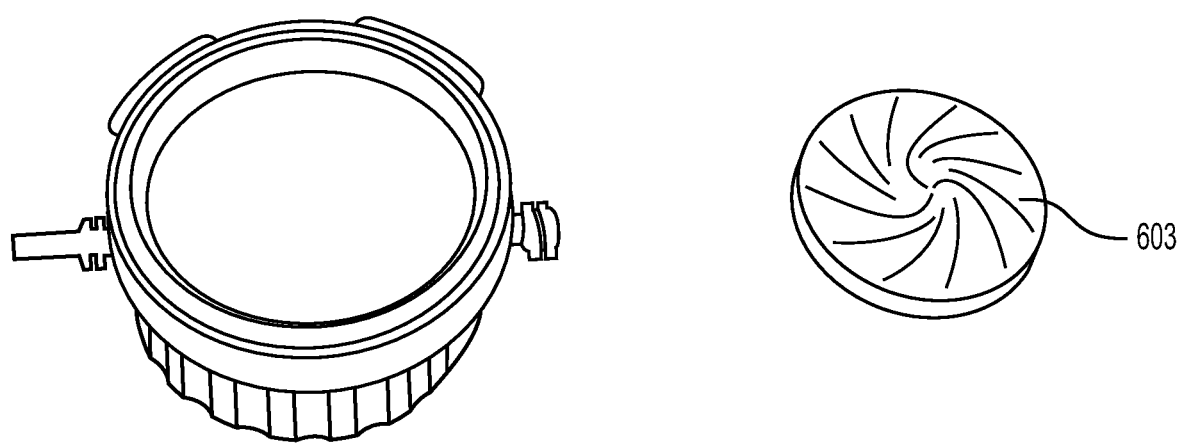

FIG. 11A shows a close-up photograph of the assembly 409. FIG. 11B shows the two components of the assembly, the plastic casing with inlet 601, the opening 602 with a plug and the disk 603.

Figure 12A:
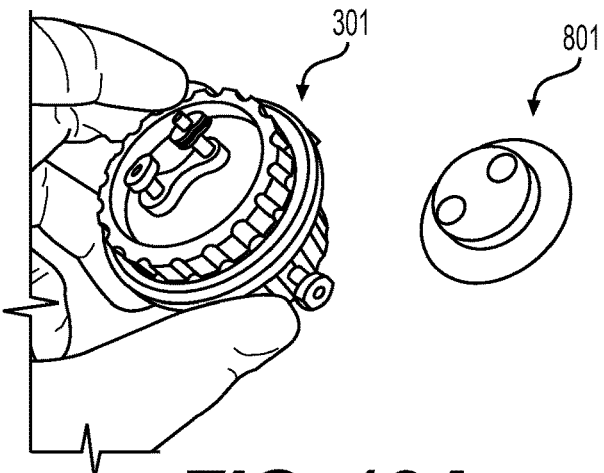
FIGS. 12A-12C illustrate the method of resuspending bacteria from a membrane filter using a rotor.

FIG. 12A shows a photograph of the exemplary dynamic microbe concentrator, and an external part 801 that is used to actuate the disk inside the concentrator via magnetic coupling.

Figure 12B:
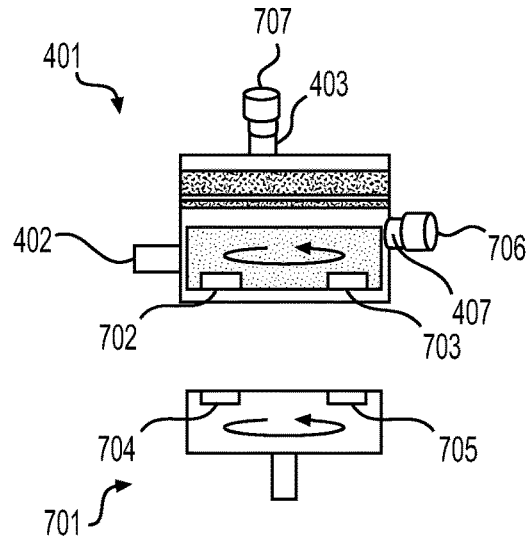
Figure 12C:
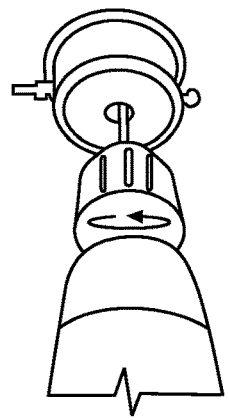

FIG. 12B shows a schematic depiction of the dynamic microbe concentrator and the external part used to actuate it. After performing dead-end microfiltration (flowing all the liquid sample past the membrane filter), outlets 403 and 407 are closed or plugged. Rotation of the external part 701 produces a rotation of the disk inside the dynamic microbe concentrator via magnetic coupling between magnets 702 and 703 in the disk and 704 and 705 in the external part. FIG. 12C shows a photograph of a drill used to rotate the external part 701, and via magnetic coupling rotate the disk 603 inside the dynamic microbe concentrator. Upon actuation, the rotation of the rotating disk exerts shear on the surface of the membrane retaining the microbe, releasing the microbe from said surface. The microbe remain in the liquid between the disk and the membrane.

Figure 13A:
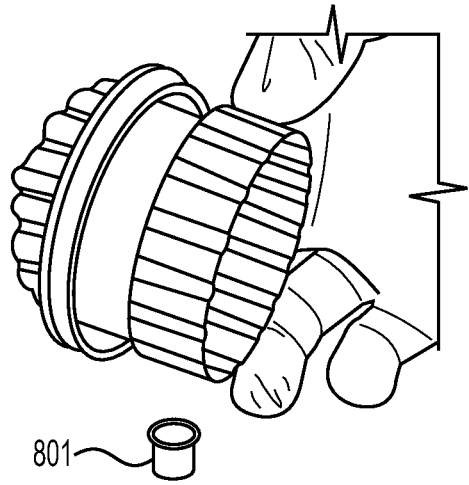
FIGS. 13A-13C illustrate the method of recovering bacteria from the dynamic microbe concentrator.
Figure 13B:
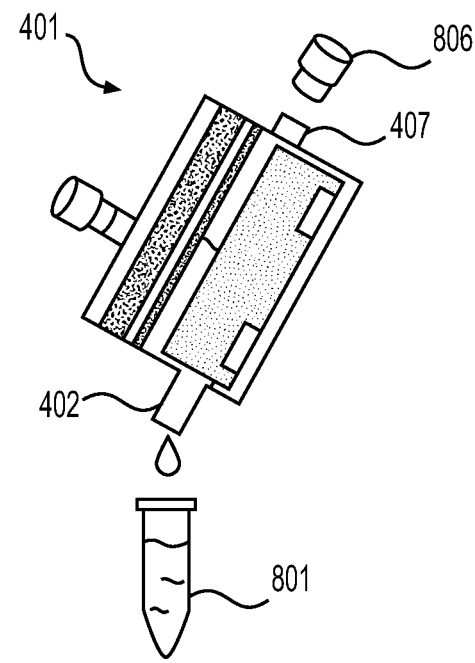
Figure 13C:
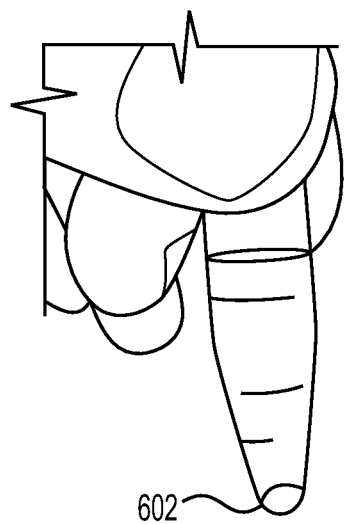

FIGS. 13A-13C show an exemplary method to harvest the microbe from the space between the disk and membrane filter inside the dynamic microbe concentrator. FIG. 13A shows a photograph during the action of harvesting the liquid containing microbe and introducing the liquid into a centrifugation vial. After the release of the microbe by rotation of the disk, the external part 701 is removed, the plug in the opening 407 is removed, and the liquid containing microbe falls by gravity and is collected in a centrifugation vial. Alternatively, pressurized air is introduced through the opening 407 to force the liquid out without the need for leveraging gravity.

FIGS. 19A-19B show a variation of the exemplary dynamic microbe concentrator depicted in FIG. 1. The principle works the same takes advantage of commercial ultrafiltration tools commonly used to sterilize liquids by ultrafiltration. FIG. 19A part 1401 is equivalent to part 409 in FIG. 9A or 9B. 1406 and 1407 are inlets/outlets, 1404 is a disk, 1408 is the cavity between the rotary part and (once mounted) the membrane filter, 1403 is a gasket and 1402 is the housing. FIG. 19B shows the individual components of the part 1401.

Figure 20C:
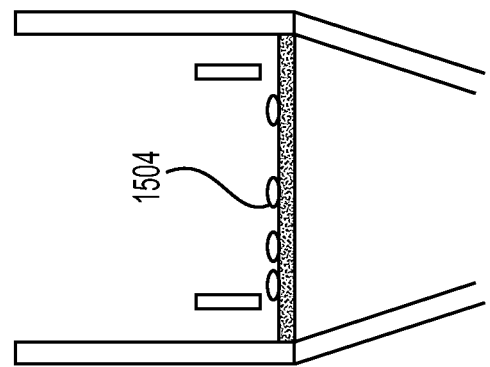
FIGS. 20A-20C illustrate a common method used to sterilize liquids by ultrafiltration.
Figure 20B:
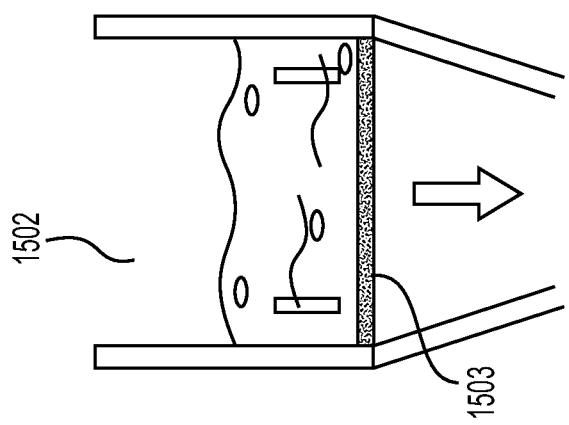
Figure 20A:
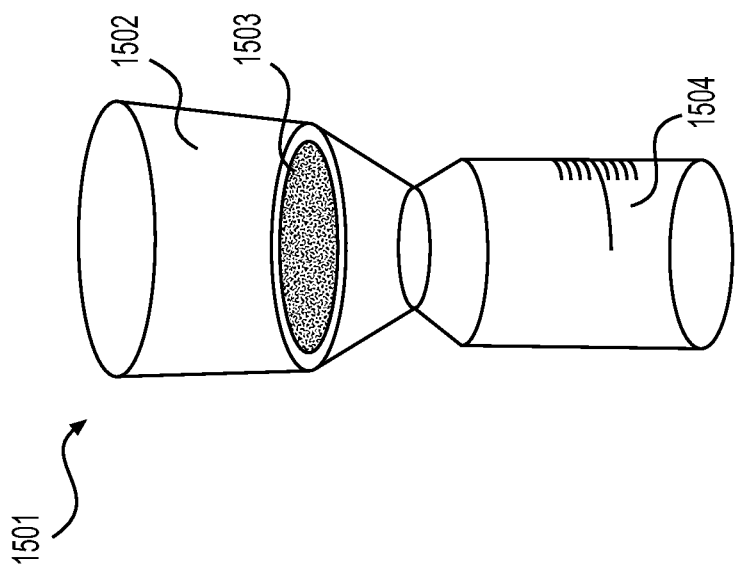

FIGS. 20A-20C and 21A-21D illustrate an additional exemplary method of operation of the present invention. FIGS. 20A-20C show a typical use of a bottle-top filtration system. Briefly, 1501 is the whole assembly of a bottle-top filtration system, 1502 is the upper container, 1504 is the lower container, 1503 is a membrane filter that separates the upper and lower container.

FIGS. 21A-21D show a typical standard operation of a commercial bottle-top filtration system. Briefly, a liquid containing microbe is introduced in 1502, vacuum applied to container 1504 drives the liquid downwards from the upper container 1502 the membrane filter 1503 towards the lower container 1504 while all the microbe and other particulates bigger than the cut-ff size of the membrane filter remain on the membrane filter's surface.

Figure 21A:
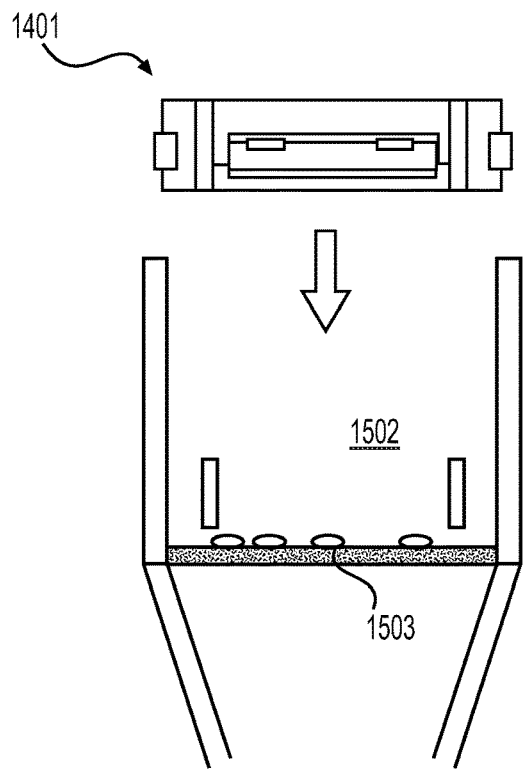
FIGS. 21A-21D illustrate a method to recover bacteria from an ultrafiltration system, using an embodiment of the dynamic microbe concentrator.
Figure 21B:
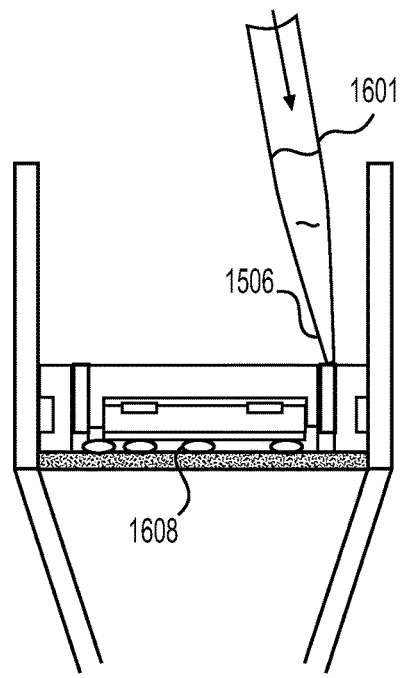
Figure 21C:
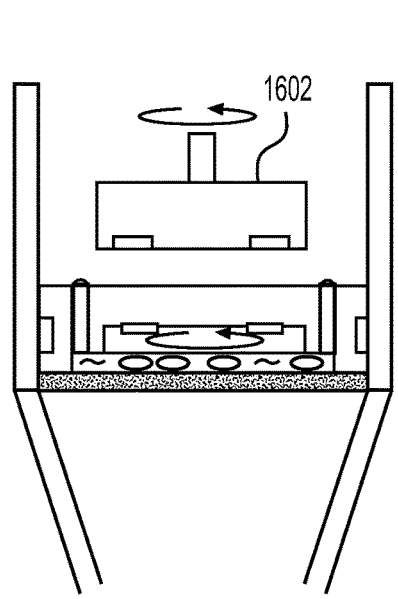
Figure 21D:
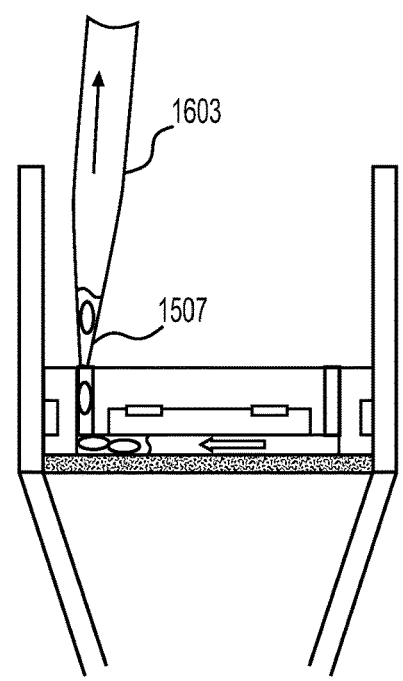

In one embodiment of the method provided herein, a liquid containing microbe is processed using a commercial bottle head operation system according to its typical standard operation, such as the method shown in FIGS. 20A-20C. Next, the part 1401 is introduced in the upper container and pressed down until it reaches the membrane filter 1503. The gasket 1403 acts as a seal for the assembly and fixes the position of part 1401. Sterile liquid is introduced through opening 1505 filling the cavity 1608 (FIG. 21B). The disk inside the dynamic microbe concentrator is rotated via magnetic coupling to an external rotating part 1602. The rotation of the rotary part imparts shear stress on the liquid in the cavity 1608, releasing the microbe from the surface of membrane filter 1503. Finally, the liquid containing microbe in cavity 1508 is recovered. The liquid is introduced in a vial, centrifuged, and the pellet is analyzed for microbe presence using standard methods such as plating in selective agar, with a molecular method such as qPCR or with a biosensor.

EXAMPLES

Example 1: Pass-Through Rate and Recovery Rate of Various Membrane Filters

This experiment was conducted to determine the pass-through rate and recovery rate of filters with various materials and pore sizes. Briefly, a membrane filter was mounted on a filter holder. One milliliter of liquid containing 200 CFU of *E. coli* O157:H7 was passed through the membrane filter, followed by 1.5 ml of water and then air. The filtrate was directly poured onto an agar plate, dried and incubated over night at 37° C. The membrane was back flushed with 1.5 ml distilled water and the liquid was directly poured into another agar plate. Each experiment was performed in triplicate. The table below shows, for each membrane, the percentage of bacteria that passed through the filter, referred to as the pass-through rate, and the percentage that was recovered by back flushing, referred to as the recovery rate.

TABLE 1

The pass-through rate and recovery rate of various membrane filters

| Material | Pore size (μm) | Pass-through rate | Recovery rate |
| --- | --- | --- | --- |
| Cellulose | 6 | 30% | 22% |
| Cellulose | 8 | 69% | 7% |
| Cellulose | 10 | 88% | 5% |
| Cellulose | 20 | 97% | 4% |
| Cellulose acetate | 5 | 75% | 8% |
| Glass fiber | 5 | 52% | 28% |
| Glass fiber | 10 | 83% | 3% |
| MCE | 5 | 24% | 21% |
| MCE | 8 | 76% | 15% |
| Nylon | 5 | 37% | 42% |
| Nylon | 10 | 84% | 2% |
| PCTE | 0.8 | 17% | 20% |
| PCTE | 2 | 86% | 1% |
| PCTE | 5 | 73% | 4% |
| PCTE | 10 | 82% | 2% |
| PCTE | 20 | 75% | 0% |
| PCTE | 30 | 82% | 1% |
| PES | 0.65 | 0% | 24% |
| PES | 1.2 | 0% | 25% |
| PES | 5 | 92% | 6% |
| Polyester track etched | 5 | 99% | 1% |
| Polyester track etched | 10 | 99% | 1% |
| Polypropilene | 5 | 83% | 3% |
| Polypropilene | 10 | 82% | 3% |
| PTFE Hydrophilic | 5 | 31% | 33% |
| PTFE Hydrophobic | 5 | 85% | 1% |
| PVDF | 3 | 3% | 75% |
| PVDF | 5 | 2% | 91% |

Surprisingly, membranes with cut off bigger than the microbe size still can be used to concentrate and recover microbe by back flushing with high efficiency. As shown in Table 1, PVDF 5 μm, PVDF 3 μm, PTFE hydrophilic 5 μm, PES 1.2 μm, Nylon 5 μm, Glass fiber 5 μm, Cellulose 6 μm, etc., all showed satisfactory pass-through rate and recovery rate. These results are surprising because the choice of the membrane filter is counterintuitive. One skilled in the art would have chosen a membrane filter with a cut-off pore size smaller than the size of the microbe to be filtered in order to collect the microbe. Instead, the present invention uses membrane filters with cut-off pore sizes bigger than the size of the microbe to be collected. As an example shown here, the present invention utilizes a PVDF membrane filter with a pore size of 5 μm to catch *E. coli* O157: H7 or *Salmonella* with an average size in the range around 0.8 μm and length around 3 μm or less.

The advantage of using larger pores is that they allow higher flow rates for the same pressure and that they tend to clog less. Membrane filters that allow passing as many microbes as possible would be ideal pre-filters, i.e., the filtration filter. Filters that allow to recover a high percentage of microbe and have large pores to prevent clogging would be ideal for concentrating the microbe, i.e., the concentration filter. Clogging is relative to the amount of small particles in suspension, and thus the ideal pore size of the membrane will depend on the food matrix.

The optimal combination of pre-filter and concentrating filter will depend on the food matrix. For example, the combination of a nylon membrane with 10 μm pores as the filtration filter and a PVDF membrane with 5 μm pores as the concentration filter works for most purposes. Surprisingly, it is possible to use a PCTE membrane with 2 μm size pores as the filtration filter, and a concentrating membrane PVDF with 5 μm size pores as the concentration filter. In the combination, 86% of the bacteria passed through the filtration filter with the smaller pores, and 91% of those bacteria were trapped and recovered by back-flushing in the concentration filter with the bigger pores.

Example 2 Recovery of Microbe from Lettuce

In this Example, a test sample of 25 grams of lettuce is mixed with 225 ml of liquid. The liquid can be bacterial broth or deionized water, etc. The sample and the liquid can be incubated from 30 min to 10 hours, preferably about 4 hours, at the optimal growth temperature specific to a microbe, such as 37° C., 35° C., or 42° C., etc. The incubation step is optional. The liquid in the sample can be pumped through two filters into a waste container. The filtration filter supports the flow through of the test sample and holds large particles of the test sample. The first membrane filter is made of nylon. The pore size of the membrane filter is 10 μm. But the pore size of the first membrane filter can be between 3 μm to 50 μm. The concentration filter supports the flow through of the test sample and holds the microbes from the test sample. The second membrane filter is made of PVDF. The pore size of the membrane filter is 5 μm. But the pore size of the second membrane filter can be between 1 μm to 10 μm.

After passing the liquid through the filters, the concentration filter is disassembled, 1.5 ml of deionized water is pumped backwards, in the direction opposite to the filtration direction used previously. The 1.5 ml of liquid pumped backwards constitutes the concentrate. The concentrate is then introduced into a vial, centrifuged typically at about 22 G. The supernatant is discarded. The pellet is the final concentrate that is analyzed with a molecular method such as qPCR or selective plating to detect specific microbes.

Example 3: Tests Performed with the Apparatus Described Herein

This experiments utilized flexible sealable containers, such as Ziploc® bags or Whirl-Pack® like bags, which were fabricated with a first pre-filter. The filtration filter was typically Nylon with 10 μm in pore size. The flexible sealable containers were used with or without a second pre-filter. The second pre-filter was typically Cellulose with 20 μm, 10 μm, or 8 μm in pore size. The pre-filters were followed by a one-way valve and a concentration filter. The concentration filter was typically made of PVDF with 5 μm in pore size. Other combinations of pre-filters and concentrating filters have also been used.

The experiments consisted of inoculating a sample (18 g, 25 g, 200 g, or 375 g) with about 10 μl of buffer containing between 200 to 1000 CFUs of *Salmonella Typhimurium* or *E. coli* O157:H7, both of which are kanamycin resistant. Next, the sample was introduced into a Pathotrak bag, a buffer was added to the bag to reach the volume as shown in Table 2 below. Next, the bag was introduced into pressure chamber and connected to the outlet. Close the pressure chamber and pressurize to 60 psi with pressurized air. Typically all the liquid was extracted from the bag and out to waste within 4 minutes. After that the pressured chamber was depressurized, the bag was removed. The concentrating filter was removed from the bag and 1.5 ml of distilled water was flushed back from the concentrator outlet through the membrane and into an agar plate with Kanymiacin (results plate). The plate was dried until there was no liquid and set to incubate at 37° C. for 12 hours. The same volume of bacteria used for inoculating the samples was also inoculated directly on plates as control (control plate). The average efficiency presented in Table 2 was calculated by dividing the total number of CFUs in the results plate by the total number of CFUs in the control plate. The controls were performed duplicate or triplicate for each experiment.

TABLE 2

Recovery efficiency for various food samples

| Sample | Sample size | n | Volume | Average efficiency | | Std |
|---|---|---|---|---|---|---|
| Romaine lettuce | 25 g | 6 | 225 ml | 33.9% | +− | 9.6% |
| Romaine lettuce | 200 g | 1 | 600 ml | 9.1% | | |
| Beef sliced | 25 g | 2 | 225 ml | 18.3% | +− | 1.5% |
| Beef sliced | 375 g | 1 | 1000 ml | 21.0% | | |
| Mushrooms | 25 g | 2 | 225 ml | 7.7% | | |
| Blackberries | 25 g | 4 | 225 ml | 18.2% | +− | 12.79% |
| Raspberries | 25 g | 4 | 225 ml | 15.2% | +− | 4.5% |
| Strawberries-sliced | 25 g | 2 | 225 ml | 6.9% | +− | 3.24% |
| Cilantro | 18 g | 2 | 225 ml | 4.3% | +− | 0.8% |

Example 4: Separation of *Salmonella* from 325 g of Ground Meat

Figure 14A:
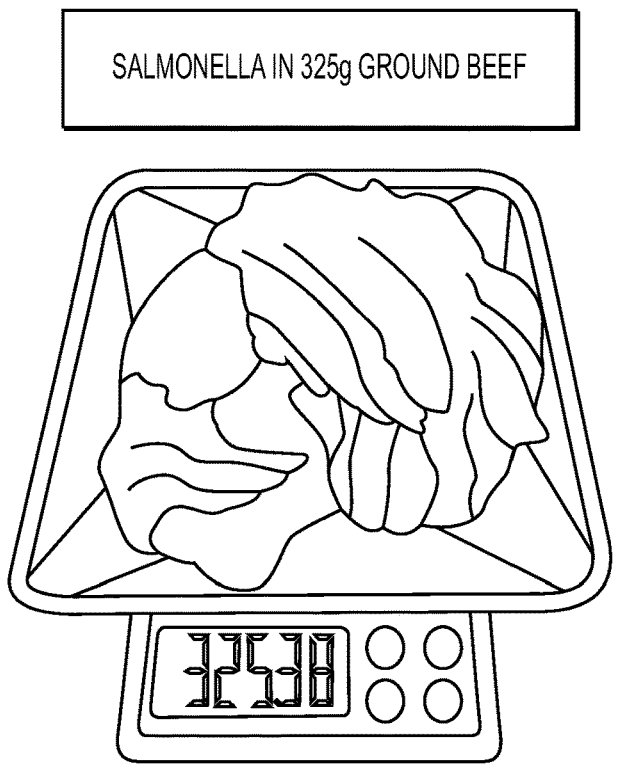
FIGS. 14A and 14B are photographs showing a 325 g ground-beef sample and a MACE separator used in combination of a dynamic microbe concentrator to separate and concentrate *Salmonella* for detection experiments.
Figure 14B:
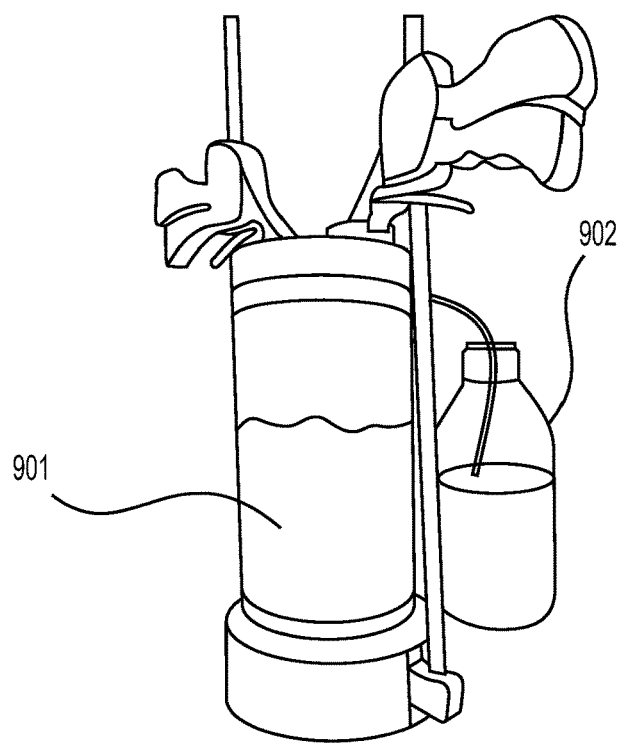
Figures 15A, 15B, 15C:
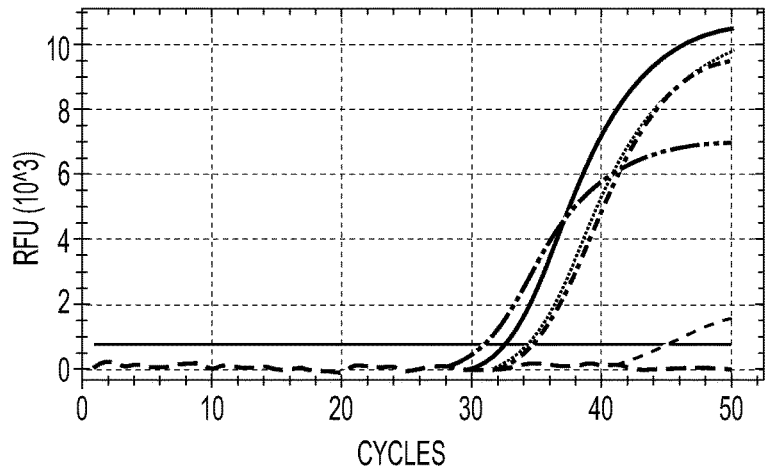
FIGS. 15A-15C show the results of using qPCR detection in combination with MACE separation and dynamic bacterial concentration for the detection of *Salmonella* in 325 g of ground beef.

Example 1 demonstrates the application and results of operating a MACE separator in combination with a dynamic microbe concentrator for separating, harvesting and detecting *Salmonella typhimurium* in about 325 g of ground beef. The set-up is shown in FIG. 14A-14B, and the results are shown in FIG. 15A-15C.

I. Methods

A MACE separator with internal volume of 850 ml was used in these experiments. A 0.45 pore size polyethersulfone (PES) membrane was used as the bottom membrane. A 10-micron size pore PCT membrane (PCT3014220 Sterlitech, Wash., USA) was used as top membrane. The PES and PCT membranes are commercially available from, for example, MilliporeSigma (Germany) or Thermo Fisher Scientific (Grand Island, N.Y.). The dynamic concentrator was built with a plastic casing fabricated by injection molding, and the disk was fabricated by 3D printing. Two discal magnets were glued to two same-size cavities of the disk. Several types of membranes were tested for the dynamic concentrator. In this experiment a PES membrane filter was used with 1.2 μm pore size purchased from Sterlitech, Wash., USA.

20 μL of an overnight culture of bacteria *Salmonella typhimurium* was diluted into 980 μl of LB. This sample was further diluted 3 times in a ration 1:10. The last dilution is the 'base solution'. The artificially contaminated sample was prepared by pipetting 20 μL of the base solution into about 325 g of ground beef FIG. 14A and letting it to rest until it was fully absorbed (typically 30 min). To determine the actual bacterial concentration inoculated in the ground meat, another aliquot of 20 μL of the base solution was pipetted as 5 ul drops into an agar plate. The plate was incubated overnight, and single colonies were counted.

A peristaltic pump was used to introduce tap water with 2% TWEEN 20 through the bottom of a MACE separator until the liquid wetted the bottom membrane filter. Subsequently, the pump was stopped, the artificially contaminated sample was introduced into the MACE separator 901, right on top of the membrane filter. A second (top) membrane filter was placed on top of the MACE separator and fixed with the MACE separator's lid. The peristaltic pump was turned on and approximately 2 L of a solution 2% TWEEN 20 in tap water was flowed past the MACE separator and out into a 2 L Glass bottle 902 prefilled with 20 ml of Tween 20 and 10 g of Serine Protease (Carolina Biological, Burlington, N.C., USA). The glass bottle was maintained 45 C throughout the separation. The content of the glass bottle was continuously mixed with a magnetic stir bar. The whole procedure of separation was performed in 20 min—the max speed of the peristaltic pump.

After separation, the liquid in the glass bottle was pumped through the dynamic concentrator. The concentration procedure was performed at the max speed of the peristaltic pump for about 20 minutes. Subsequently approximately 400 ml of DI water (sterile) was pumped through the concentrator to remove the protease and TWEEN 20. Finally, the outlet of the concentrator was plugged close, the peristaltic pump removed, and the disk inside the dynamic concentrator was rotated at approximately 400 rpm for 10 seconds to create shear on the membrane filter holding the bacteria (inside the concentrator). Thereafter, the external part was removed, the inlet of the concentrator was aligned with a centrifuge vial, and the plug of second outlet was removed, to allow the liquid between the disk and the membrane filter to fall into the vial due to the action of gravity. Finally, the vial was centrifuged at 22 G, the supernatant was discarded, the pellet (approx. 10 ul) of liquid was vortexed, and 5 μl of this concentrated sample was introduced into a qPCR vial from Bio-rad containing the mastermix and fluorescent probes for *Salmonella* spp. A negative and positive control were also prepared according to Bio-rad's instructions. Two more qPCR vials were loaded with master mix, fluorescent probes and 5 μl of the initial pure dilutions 10-2 and 10-3 as controls.

II. Results

Each droplet of 5 μl of the 1:10 dilution of the base solution contained 26.8±3.1 CFU by plating and colony counting. Therefore, the bacterial concentration of the base solution was 268±31 CFU/5 ul, and the bacterial count in approximately 325 g artificially contaminated ground beef was 1075±129 CFU. 10 μl of liquid was recovered containing concentrated bacteria from the 325 g of artificially contaminated ground beef as detailed in the protocol (methods).

The results of the test are provided in FIGS. 15A-15C. FIG. 15A shows the arrangement of qPCR vials inside the qPCR instrument from Bio-rad. 'ext' corresponds to 5 µl (out of the 10 µl recovered) of concentrated bacteria by using the MACE separation in combination with the dynamic microbe concentrator. B02 and B03 are two replicates of the same experiment. B04 and B05 correspond to duplicate controls each having 5 ul of the pure base solution, and B06 and B07 corresponds to duplicate controls each having 5 ul of the pure base solution diluted in LB 1:10. B08 and B09 are positive and negative controls respectively. FIG. 15B shows the results after running the qPCR instrument for approximately 2 hours. The last column shows the positive detection of *Salmonella* DNA in the pure culture controls (B04-B07), positive detection in Bio-rad's positive control (B08), positive detection in the two duplicates of concentrated bacteria from the artificially contaminated ground beef (B02 and B03), and negative detection in Bio-rad's negative control (B09). Column Cq target shows the qPCR cycle at which the instrument detected *Salmonella* DNA, and Cq internal control shows the qPCR cycle at which the instrument detected (or did not detect) the control DNA present in all the samples. FIG. 15C shows the temporal evolution of the signal obtained by the instrument in each qPCR vial, and the threshold signal at which the Cq targets were calculated.

III. Discussion

In previous experiments several types of membranes were tested to optimize the performance of the MACE separator. Using a high flow membrane filter such as a PES with pores slightly bigger (1.2 µm) than the bacterial size (typically 0.4-0.8 diameter) could be optimal for the separation because it would allow the bacteria to pass through the pores and retain particles bigger than 1.2 µm in diameter. Surprisingly bacteria with diameter 0.4-0.8 µm also were also trapped in the high flow PES membranes with 1.2 um size pores. PES membranes are composed of a mesh of fibers and do not have well defined pores such as track etched membranes, soPES was used as the membrane filter inside the dynamic microbe concentrator. Other track etched membranes tested inside dynamic microbe concentrator were prone to clog, the PES membrane with cut off 1.2 µm worked perfect for the liquid volumes tested, and allowed us to recover the bacteria from the cavity between disk and membrane filter without issue. Therefore, all the experiments here presented were performed with a dynamic microbe concentrator having a PES membrane filter with 1.2 µm size pores.

The results presented in FIGS. 15A-15C demonstrate the principle for the positive detection in 40 min of 1075±129 CFU of *Salmonella* in approximately 325 g of ground beef sample artificially contaminated, by using the MACE separation, enzymatic digestion, dynamic concentration and qPCR detection.

The experiments were not designed to establish the Limit of Detection (LoD) of the whole protocol. However, since 10 µl of concentrated bacteria was recovered and split into two aliquots of 5 µl µl for detection, and both were positive, the results suggest that the LoD is at least as low as 537.5±64.5 CFU/325 g of ground beef. Ground beef is one of the most complex meat samples to be assayed because of the small size of its protein and fat constituents. Larger size meat portions such as in trims are simpler to assay with the methods of the disclosure.

The Cq internal control was not detected for the sample with concentrated bacteria. This means that there were proteins and other substances present in the concentrate that interfered with qPCR detection. This interference did not prevent positive detection of *Salmonella*, and it indicates that optimization of the enzymatic digestion of the concentrate will result in faster and more sensitive *Salmonella* detection.

Since the protocol does not exploit any special properties of *Salmonella* bacteria except for size, it is expected that the same protocol will yield similar results with other bacteria or virus with similar or smaller size.

The lowest bacterial load tested here is compatible with current efforts to determine the *Salmonella* load of 325 g of Ground Turkey and ground beef. The results suggest that a short incubation period prior to separation, during separation or even after concentration, will bring down the LoD of the protocol to 1 CFU/325 g of ground beef, and meet the USDA regulations for Ecoli O157:H7 and STEC for ground beef and trims.

Notably, standard protocol was not used for adding detergents and cycling the temperature of the extracted bacteria for DNA extraction prior to the introduction of a subsample into the qPCR vials. This lengthy step was not required because the sample was rinsed with DI water inside the dynamic microbe concentrator before the bacteria were harvested.

Figure 16A:
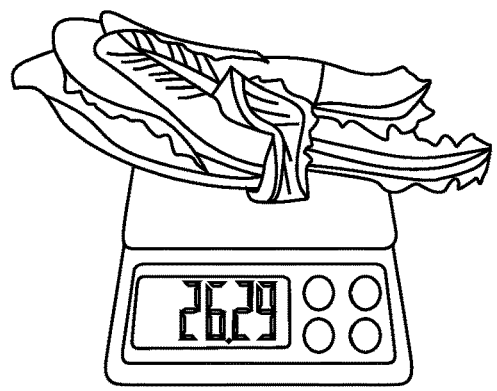
FIGS. 16A and 16B are photographs showing 25 g romaine lettuce sample and a MACE separator used in combination of a dynamic microbe concentrator to separate and concentrate O157:H7 and *Salmonella* for detection.
Figure 16B:
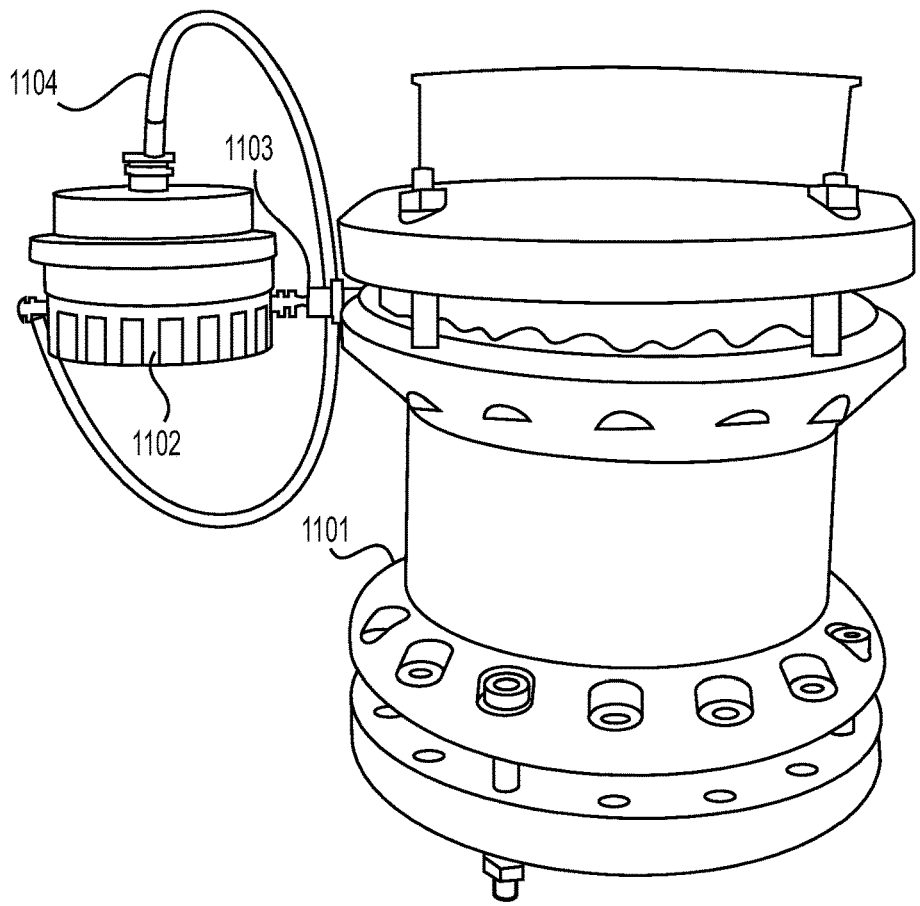

Example 5: Separation of *Salmonella* and *E. coli* O157:H7 from 25 g of Romain Lettuce Example 2 demonstrates the application and results of operating a MACE separator in combination of the dynamic concentration for separating *E. coli* O157:H7 from about 25 g of romaine lettuce. The set-up is shown in FIGS. 16A-16B, and the results are shown in FIGS. 17A-17C and FIGS. 18A-18C.

I. Methods

A MACE separator with internal volume of 425 ml was used in these experiments. A 0.45 pore size polyethersulfone (PES) membrane was used as the bottom membrane. A 10-micron size pore PCTE membrane (PCT3014220 Sterlitech, Wash., USA) was used as top membrane. The PES and PCT membranes are commercially available from, for example, MilliporeSigma (Germany) or Thermo Fisher Scientific (Grand Island, N.Y.). The same dynamic microbe concentrator from Example 1 was used, after the concentrator was cleaned, sterilized and assembled with new PES sterile membrane filter.

Preparation of artificially contaminated samples. 20 µL of an overnight culture of bacteria *Salmonella typhimurium* was diluted into 980 µl of LB. This sample was further diluted 5 times in a ration 1:10. Dilutions 3, 4 and 5 are referred to as the '*Salmonella*-3 base solution', '*Salmonella*-4 base solution' and '*Salmonella*-5 base solution'. Additionally, 20 µL of an overnight culture of bacteria *E. coli* O157:H7 was diluted into 980 µl of LB. This sample was further diluted 5 times in a ration 1:10. Dilutions 3, 4 and 5 are referred to as the 'O157:H7-3 base solution', 'O157:H7-4 base solution' and 'O157:H7-5 base solution'. Three independent tests were performed for dilutions-3, -4 and -5 of *E. coli* and *Salmonella* combined. Briefly, the first artificially contaminated sample (first sample) was prepared by pipetting four times 5 µL (total 20 µL) of *Salmonella* base solutions-3, and four times 5 µL (total 20 µL) of O157:H7 base solutions-3 on different locations of the surface of a 25 g sample of romaine lettuce The sample was let to rest inside a bio-safety hood until the drops dried up on the lettuce surface (typically 2 h). To determine the actual bacterial concentration inoculated on the sample's surface, five drops of 20 μL of the *Salmonella*-5 base were pipetted on a first agar plate and five drops of 20 μL of the O157:H7-3 base solution were pipetted onto a second agar plate. The plates were incubated overnight, and single colonies were counted.

The second contaminated sample (second sample) was prepared with the same protocol as the first sample, with the exception that *Salmonella*-4 base solution and O157:H7-4 base solution were used instead of *Salmonella*-3 base solution and O157:H7-3 base solution. The third artificially contaminated sample (third sample) was prepared with the same protocol as the first sample, with the exception that *Salmonella*-5 base solution and O157:H7-5 base solution were used instead of *Salmonella*-3 base solution and O157:H7-3 base solution. Separation protocol: the first sample was chopped into 1 inch by 1 inch pieces, and introduced into a plastic glass containing DI water. The glass was placed in a vacuum jar and vacuum was applied for 10 seconds.

A peristaltic pump was used to introduce tap water with 2% Tween 20 through the bottom of a MACE separator until the liquid wetted the bottom membrane filter. Subsequently, the pump was stopped, the first sample in DI water was introduced into the MACE separator, right on top of the membrane filter. A second (top) membrane filter was placed on top of the MACE separator and fixed with the MACE separator's lid. The peristaltic pump was turned on and 1 L of Tap water with 2% Tween was flowed past the MACE separator out into the dynamic microbe concentrator directly, without adding digestive enzymes. The procedure was performed in 20 min—max speed of the peristaltic pump—and the pressure drop was recorded as <1 PSI. Finally, the outlet of the concentrator was plugged close, the USB concentrator was removed from the MACE separator and the disk inside the dynamic microbe concentrator was rotated at approximately 400 rpm for 10 seconds to create shear on the cavity of the dynamic microbe concentrator between filter and disk and release the bacteria from the filter. The rotation of the movable part was accomplished using a drill (home depot) operated at max. low speed, in conjunction with an external part. The rotation of the external part produced the same rotation of the internal movable part by magnetic coupling. Thereafter, the external part was removed, the inlet of the concentrator was aligned with a centrifuge vial, and the plug of second outlet was removed, to allow the liquid between the movable part and the membrane to fall into the vial due to the action of gravity. The vial was centrifuged at 22 G, the supernatant was discarded and the vial with the pellet (approx. 10 μl) of liquid was reserved kept in ice until qPCR detection.

The separation/concentration protocol was repeated for second and third samples, and after each experiment the vial with the pellet was kept in ice until qPCR detection. Finally, the vial corresponding to the concentrate from the first sample was vortexed and centrifuged at low speed (60 rpm); 5 μL of this first concentrated sample was introduced into a qPCR vial from Bio-rad containing the mastermix and fluorescent probes for *Salmonella*, and 5 μl of the concentrated sample was introduced into a qPCR vial from Bio-rad containing the mastermix and fluorescent probes for *E. coli* O157:H7. The same operation was performed with the vial from the second sample and the vial from the third sample. A negative and positive control were also prepared according to Bio-rad's instructions. One more control experiment was performed in the same way as the protocol used in the first, second and third sample with the exception that no *Salmonella* or O157:H7 bacteria were introduced in the sample. This control assay is the 'blank sample'.

II. Results

Plating and colony counting that the number of *Salmonella* bacteria in 20 μl of *Salmonella*-5 base solution was 16.0±1.8 CFU. Therefore, the third sample was inoculated with 16.0±18 CFU of *Salmonella*, the second sample was inoculated with 160±18 CFU of *Salmonella* and the first sample was inoculated with 1600±180 CFUs of *Salmonella*. Plating and colony counting that the number of O157:H7 bacteria in 20 μl of O157:H7-5 base solution was 7.0±1.7 CFU. Therefore, the third sample was inoculated with 7.0±1.7 CFUs of O157:H7, the second sample was inoculated with 70±17 CFUs of O157:H7 and the first sample was inoculated with 700±170 CFUs of O157:H7. Approximately 10 μl of liquid was recovered from the first sample, second sample and third sample, containing concentrated bacteria from the three 25 g of artificially romaine lettuce as detailed in the protocol.

Figures 17A, 17B, 17C:
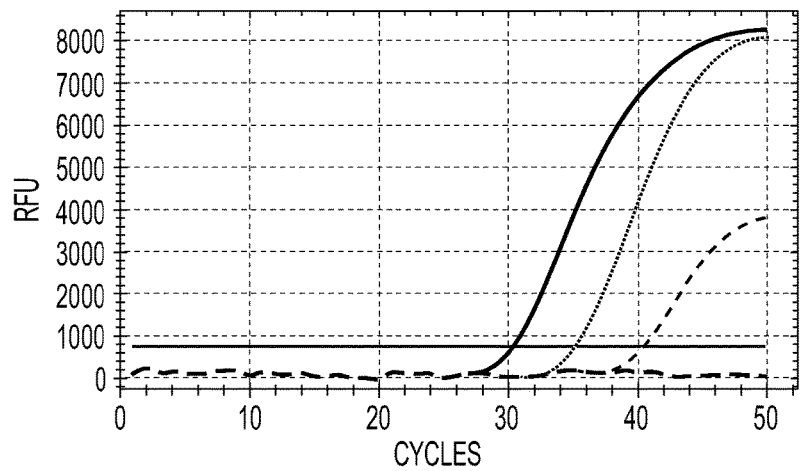
FIGS. 17A-17C Show the results of using PCR detection in combination with MACE separation and USB concentration to detect *E. coli* O157:H7 in 25 g of romaine lettuce.

The results of the O157:H7 test are provided in FIGS. 17A-17C. FIG. 17A shows the arrangement of qPCR vials inside the qPCR instrument from Bio-rad. C02 'blank' corresponds to 5 μl (out of the 10 μl recovered) of concentrated bacteria from the MACE separation in combination with the dynamic microbe concentrator when the approximately 25 g sample of romaine lettuce was not artificially contaminated. C03'-5', C04'-4' and C05'-3' correspond to testing 5 μl (out of the 10 μl recovered) of three independent experiments with 25 g of romaine lettuce inoculated with 7.0±1.7 CFU, 70±17 CFUs and 700±170 CFUs respectively. C06 'Pos ctrl' corresponds to a positive control and C07 'Neg ctr' a negative control, both according to Bio-rad's instructions.

FIG. 17B shows the results after running the qPCR instrument for approximately 2 hours. The last column shows that the positive and negative controls were valid, the blank test (test control) was also valid—no detection of O157:H7 in the blank experiment, and positive detection of O157:H7 DNA in two of the three dilution experiments of artificially contaminated romaine lettuce (C04, C05) and negative detection in the lowest dilution experiment corresponding to 7.0±1.7 CFU. Column Cq target shows the qPCR cycle at which the instrument detected O157:H7 DNA, and Cq internal control shows the qPCR cycle at which the instrument detected (or didin't detect) the control DNA present in all the samples. FIG. 17C shows the temporal evolution of the signal obtained by the instrument in each qPCR vial, and the threshold signal at which the Cq targets values were calculated.

Figures 18A, 18B, 18C:
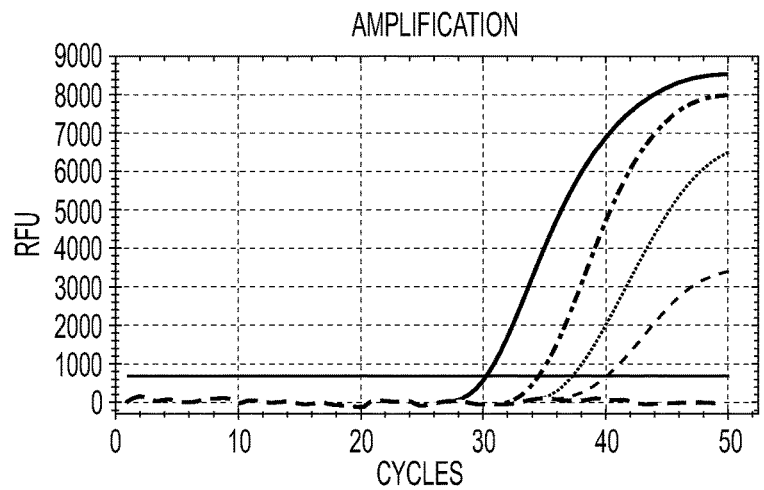
FIGS. 18A-18C Show the results of using PCR detection in combination with MACE separation and USB concentration to detect *Salmonella* in 25 g of romaine lettuce.

The results of the *Salmonella* test are provided in FIGS. 18A-18C. FIG. 18A shows the arrangement of qPCR vials inside the qPCR instrument from Bio-rad. C02 'blank' corresponds to 5 μl (out of the 10 μl recovered) of concentrated bacteria from the MACE separation in combination with the dynamic microbe concentrator when the 25 g sample of romaine lettuce was not artificially contaminated. C03'-5', C04'-4' and C05'-3' correspond to testing 5 μl (out of the 10 μl recovered) of three independent experiments with 25 g of romaine lettuce inoculated with 16.0±1.8 CFU, 160±18 CFUs and 1600±1800 CFUs respectively. C06 'Pos ctrl' corresponds to a positive control and C07 'Neg ctr' a negative control, both according to Bio-rad's instructions.

FIG. 18B shows the results after running the qPCR instrument for approximately 2 hours. The last column shows that the positive and negative controls were valid, the blank test (test control) was also valid—no detection of *Salmonella* in the blank experiment, and positive detection of *Salmonella* DNA in the three dilution experiments of artificially contaminated romaine lettuce (C03-C05). Column Cq target shows the qPCR cycle at which the instrument detected *Salmonella* DNA, and Cq internal control shows the qPCR cycle at which the instrument detected (or didin't detect) the control DNA present in all the samples. FIG. 18C shows the temporal evolution of the signal obtained by the instrument in each qPCR vial, and the threshold signal at which the Cq targets values were calculated.

III. Discussion

These results demonstrate principle of the positive detection in 2 h 20 min of 16.0±1.8 CFU of *Salmonella* and 70±17 CFUs of O157:H7 in a 25 g of romaine lettuce sample artificially contaminated, by using the MACE separation, dynamic concentration and qPCR detection.

The experiments were not designed to establish the Limit of Detection (LoD) of the whole protocol. However, since 10 µl of concentrated bacteria was recovered and split the 10 µl into two aliquots of 5 µl, one used to detect *Salmonella* and the other to detect O157:H7, the results suggest that the LoD is at least as low as 8±0.9 *Salmonella* CFUs and 35±8.5 CFUs of O157:H7 in a 25 g romaine lettuce sample. Notably, enzymatic digestion of Romaine Lettuce components was not used (e.g. pectine or cellulase). Additionally, other tests had similar results even if the MACE separator was flipped horizontally. This means that microfiltration counterflow to sedimentation is not necessary for separation of concentration of microbes from romaine lettuce (flipping the MACE separator when the sample is ground meat clogs the membranes almost instantly making the separation impossible). Furthermore, these results indicate that the dynamic microbe concentrator can be used independently to the MACE separator depending on the properties of the original sample.

Since the protocol does not exploit any special properties of the microbes except for size, it is expected that the same protocol will yield similar results with other bacteria or virus with similar or smaller size.

It is estimated that pre-incubation of the sample of about 1 hour should be enough to allow the growth of a single CFU present in the sample into around 100 CFUs that could be detected directly according to the protocols detailed earlier. This will bring the total time for detecting a single CFU in the sample to 3 hours 20 min using the same qPCR instrument used in the experiments. Other qPCR instruments exist that provide results in 1 hour instead of 2 hours. The system of the disclosure will enable detection of 1 CFU of *Salmonella* or O157:H7 in 25 g of romaine lettuce in 3 h 20 min.

What is claimed is:

1. An apparatus, comprising:
   one or more sealable containers configured to receive a test sample comprising a liquid portion,
   at least one outlet port, and
   at least one filtration filter and at least one concentration filter fluidly connected in sequence, a filtrate from the at least one concentration filter being provided to the at least one outlet port to form a filtered outlet port,
   wherein after the one or more sealable containers is sealed, the apparatus is configured to permit flow of the liquid portion of the test sample from the one or more sealable containers through the at least one filtered outlet port via the at least one filtration filter and the at least one concentration filter when a pressure difference of equal to or greater than about 4 pounds per square inch (psi) exists between the one or more sealable containers and the filtered outlet port,
   wherein the test sample comprises or is suspected to comprise a microbe, and
   wherein each of the at least one filtration filter and the at least one concentration filter has a pore size equal to or greater than the average size of the microbe.

2. The apparatus of claim 1, further comprising one or more inlets.

3. The apparatus of claim 2, wherein the filtered outlet port comprises flexible tubing.

4. The apparatus of claim 1, further comprising
   a collection vessel configured to receive at least a fraction of the liquid portion of the test sample after it passes through the filtered outlet port.

5. The apparatus of claim 1, wherein the one or more sealable containers is housed in a pressurized chamber.

6. The apparatus of claim 4,
   wherein the collection vessel is not housed in a pressurized chamber, and
   wherein there is a pressure differential between the ambient pressure surrounding the one or more sealable containers and the ambient pressure within the collection vessel that causes liquid to flow from the one or more sealable containers, through the filtered outlet port and into the collection vessel.

7. The apparatus of claim 6, wherein the ambient pressure within the collection vessel is about atmospheric pressure.

8. The apparatus of claim 1, wherein the apparatus is configured to permit flow of the test sample through the filtered outlet port at a pressure difference between the one or more sealable containers and the filtered outlet port that is equal to or greater than about 20 psi.

9. The apparatus of claim 1, wherein the at least one filtration filter and the at least one concentration filter are membrane filters.

10. The apparatus of claim 1, wherein the at least one filtration filter and the at least one concentration filter are independently hydrophilic or hydrophobic.

11. The apparatus of claim 1, wherein the at least one filtration filter and the at least one concentration filter independently comprise a material selected from the listing consisting of: cellulose, glass fiber, Mixed Cellulose Ester (MCE), nylon, polycarbonate, Polycarbonate Track Etch (PCTE), polyethersulfone (PES), polytetrafluoroethylene (PTFE) hydrophilic, polyvinylidene fluoride or poly vinylidene difluoride (PVDF), or a material having a microstructure substantially similar to any of the forgoing materials.

12. The apparatus of claim 1, wherein the at least one filtration filter and the at least one concentration filter comprise the same or different materials.

13. The apparatus of claim 1, wherein the at least one filtration filter and the at least one concentration filter each have a pore size equal to or greater than about 0.5 micrometers (µm) or about 1 µm.

14. The apparatus of claim 1, wherein the at least one filtration filter and the at least one concentration filter have the same or different pore sizes.

15. The apparatus of claim 1,
wherein the at least one filtration filter comprises nylon and has a pore size equal to or greater than about 5 μm, and
wherein the at least one concentration filter comprises PVDF and has a pore size in the range of about 1 μm to about 50 μm.

16. The apparatus of claim 15,
wherein the at least one filtration filter comprises nylon and has a pore size of about 10 μm, and
wherein the at least one concentration filter comprises PVDF and has a pore size of about 5 μm.

17. The apparatus of claim 1,
wherein the apparatus further comprises a one-way valve located between the at least one filtration filter and at least one concentration filter, and
wherein the one-way valve is configured to permit flow of the liquid portion of the test sample from the at least one filtration filter to the at least one concentration filter.

18. The apparatus of claim 1, wherein the one or more sealable containers is flexible or rigid.

19. The apparatus of claim 1, wherein the one or more sealable containers is configured to allow a pressure source to be applied to the test sample.

20. The apparatus of claim 19, wherein the pressure source is a plunger, a piston, an impeller, or a peristaltic pump.

21. The apparatus of claim 19, wherein the pressure source is ambient pressure surrounding the one or more sealable containers and controlled by a pressurized chamber housing the one or more sealable containers.

22. The apparatus of claim 1, wherein the apparatus has two or more sealable containers, the two or more sealable containers being fluidly connected in parallel.

23. The apparatus of claim 22, wherein the two or more sealable containers are connected by patterned constrictions.

24. The apparatus of claim 23, wherein the patterned constrictions between the two or more sealable containers creates resistance to flow among the two or more sealable containers.

25. The apparatus of claim 1, wherein the test sample comprises water, food sample, human tissue, human fluids, animal tissue, animal fluids, plant tissue, clinical sample, or an environmental sample.

26. The apparatus of claim 1, wherein the test sample comprises one or more digestive enzymes.

* * * * *